(12) United States Patent
Zhang

(10) Patent No.: US 8,345,226 B2
(45) Date of Patent: Jan. 1, 2013

(54) SPECTROMETERS MINIATURIZED FOR WORKING WITH CELLULAR PHONES AND OTHER PORTABLE ELECTRONIC DEVICES

(76) Inventor: Jingyun Zhang, Upper St. Clair, PA (US)

( * ) Notice: Subject to any disclaimer, the term of this patent is extended or adjusted under 35 U.S.C. 154(b) by 297 days.

(21) Appl. No.: 12/734,607

(22) PCT Filed: Nov. 14, 2008

(86) PCT No.: PCT/US2008/083613
§ 371 (c)(1),
(2), (4) Date: May 12, 2010

(87) PCT Pub. No.: WO2009/070459
PCT Pub. Date: Jun. 4, 2009

(65) Prior Publication Data
US 2010/0309454 A1 Dec. 9, 2010

Related U.S. Application Data

(60) Provisional application No. 61/004,959, filed on Nov. 30, 2007.

(51) Int. Cl.
*G01N 33/48* (2006.01)
(52) U.S. Cl. .................................. 356/39; 356/40
(58) Field of Classification Search ............... 356/39–42
See application file for complete search history.

(56) References Cited

U.S. PATENT DOCUMENTS

| 887,357 A | 5/1908 | Stubblefield |
| 2,723,589 A | 11/1955 | Bullock et al. |
| 3,572,933 A | 3/1971 | Boostrom |
| 3,578,866 A | 5/1971 | Kohler et al. |
| 3,625,615 A | 12/1971 | Wilson |
| 3,663,762 A | 5/1972 | Joel, Jr. |
| 3,680,957 A | 8/1972 | Fukuda |
| 3,775,010 A | 11/1973 | Chupp et al. |
| 3,888,590 A | 6/1975 | White |

(Continued)

FOREIGN PATENT DOCUMENTS
EP 1 528 380 A1 5/2005
(Continued)

OTHER PUBLICATIONS

Zeiss, "Monolithic Miniature Spectrometer—MMS 1," The 1994 Photonics Circle of Excellence Award Winners, Photonics Spectra, May 1994, p. 91.

(Continued)

*Primary Examiner* — Michael P Stafira
(74) *Attorney, Agent, or Firm* — Oliff & Berridge, PLC

(57) ABSTRACT

Based on the present invention, superior compact spectrometers may be constructed and integrated into a cellular phone, or attached to a cellular phone. Such a cellular phone may be a PDA phone, which supplies electrical power to the said spectrometer, provided with data storage, signal processing capability, and real-time display. As a combined standalone system, it allows spectroscopic measurements to be fulfilled in real-time applications in field, and results can be sent out in wireless communication to a remote station or to another cellular phone user in order to share the measurement results right away. When the system is used with a laser to function as a Raman spectrometer system, it can fulfill many daily routine tasks encountered by ordinary civilians, for example, the blood glucose monitoring for diabetes patients at home in a non-invasive manner.

80 Claims, 11 Drawing Sheets

U.S. PATENT DOCUMENTS

| | | |
|---|---|---|
| 3,906,166 A | 9/1975 | Cooper et al. |
| 3,917,403 A | 11/1975 | Chupp et al. |
| 3,923,399 A | 12/1975 | Brumley |
| 4,025,196 A | 5/1977 | Chupp et al. |
| 4,043,670 A | 8/1977 | Kozlov et al. |
| 4,225,233 A | 9/1980 | Ogan |
| 4,310,244 A | 1/1982 | Perkins et al. |
| 4,315,691 A | 2/1982 | Perkins et al. |
| 4,399,555 A | 8/1983 | MacDonald et al. |
| 4,441,815 A | 4/1984 | Izumi |
| 4,462,688 A | 7/1984 | Gold |
| 4,469,441 A | 9/1984 | Bernier et al. |
| 4,553,253 A | 11/1985 | Petersen |
| 4,568,187 A | 2/1986 | Kita et al. |
| 4,573,793 A | 3/1986 | Sasaki |
| 4,613,233 A | 9/1986 | Wilson |
| 4,623,251 A | 11/1986 | Pouey |
| 4,644,632 A | 2/1987 | Machler et al. |
| 4,652,761 A | 3/1987 | Kerr et al. |
| 4,657,390 A | 4/1987 | Doyle |
| 4,697,924 A | 10/1987 | Akiyama |
| 4,705,396 A | 11/1987 | Bergstrom |
| 4,717,254 A | 1/1988 | Masuda |
| 4,732,476 A | 3/1988 | Barshad |
| 4,743,112 A | 5/1988 | Burke |
| 4,744,618 A | 5/1988 | Mahlein |
| 4,752,130 A | 6/1988 | George et al. |
| 4,776,696 A | 10/1988 | Hettrick et al. |
| 4,784,935 A | 11/1988 | Ehrfeld et al. |
| 4,815,849 A | 3/1989 | Sullivan |
| 4,832,491 A | 5/1989 | Sharpe et al. |
| 4,838,645 A | 6/1989 | Machler et al. |
| 4,938,553 A | 7/1990 | Maerz et al. |
| 4,973,159 A | 11/1990 | Sohma et al. |
| 4,983,039 A | 1/1991 | Harada et al. |
| 4,984,888 A | 1/1991 | Tobias |
| 4,995,724 A | 2/1991 | Sonobe et al. |
| 4,997,281 A | 3/1991 | Stark |
| 4,999,489 A | 3/1991 | Huggins |
| 5,020,910 A | 6/1991 | Dunn et al. |
| 5,026,160 A | 6/1991 | Dorain et al. |
| 5,050,992 A | 9/1991 | Drummond et al. |
| 5,078,495 A | 1/1992 | Harada et al. |
| 5,122,127 A | 6/1992 | Stanley |
| 5,127,728 A | 7/1992 | Warren et al. |
| 5,139,335 A | 8/1992 | Lundeen et al. |
| 5,159,404 A | 10/1992 | Bittner |
| 5,173,748 A | 12/1992 | Bilhorn |
| 5,182,609 A | 1/1993 | Florek et al. |
| 5,192,981 A | 3/1993 | Slutter et al. |
| 5,223,913 A | 6/1993 | Ando et al. |
| 5,231,462 A | 7/1993 | Dschen |
| 5,233,405 A | 8/1993 | Wildnauer et al. |
| 5,257,086 A | 10/1993 | Fateley et al. |
| 5,260,767 A | 11/1993 | Cook |
| 5,265,158 A | 11/1993 | Tattari |
| 5,285,254 A | 2/1994 | De Sa |
| 5,305,082 A | 4/1994 | Bret |
| 5,319,437 A | 6/1994 | Van Aken et al. |
| 5,359,409 A | 10/1994 | Wildnauer et al. |
| 5,384,656 A | 1/1995 | Schwenker |
| 5,402,227 A | 3/1995 | Schuma |
| 5,424,826 A | 6/1995 | Kinney |
| 5,457,530 A | 10/1995 | Nagai |
| 5,493,393 A | 2/1996 | Beranek et al. |
| 5,497,231 A | 3/1996 | Schmidt |
| 5,504,575 A | 4/1996 | Stafford |
| 5,528,364 A | 6/1996 | Koike |
| 5,532,818 A | 7/1996 | Tokumoto |
| 5,550,375 A | 8/1996 | Peters et al. |
| 5,557,404 A | 9/1996 | Matsui et al. |
| 5,570,180 A | 10/1996 | Nagai |
| 5,631,735 A | 5/1997 | Nagai |
| 5,652,681 A | 7/1997 | Chen et al. |
| 5,657,121 A | 8/1997 | Nishina |
| 5,710,627 A | 1/1998 | Inoue et al. |
| 5,717,487 A | 2/1998 | Davies |
| 5,722,067 A | 2/1998 | Fougnies et al. |
| 5,748,310 A | 5/1998 | Fujiyoshi |
| 5,754,290 A | 5/1998 | Rajic et al. |
| 5,767,966 A | 6/1998 | Iwasaki |
| 5,781,290 A | 7/1998 | Bittner et al. |
| 5,784,159 A | 7/1998 | Iwasaki |
| 5,801,831 A | 9/1998 | Sargoytchev |
| 5,812,262 A | 9/1998 | Ridyard et al. |
| 5,818,586 A | 10/1998 | Lehto et al. |
| 5,825,484 A | 10/1998 | Iwasaki |
| 5,841,856 A | 11/1998 | Ide |
| D405,457 S | 2/1999 | Kawashima |
| 5,880,833 A | 3/1999 | Iwasaki |
| 5,880,834 A | 3/1999 | Chrisp |
| 5,909,280 A | 6/1999 | Zavracky |
| 5,923,420 A | 7/1999 | Iwasaki |
| 5,949,541 A | 9/1999 | Merle |
| 6,016,197 A | 1/2000 | Krivoshlykov |
| 6,023,330 A | 2/2000 | Marshall et al. |
| 6,057,925 A | 5/2000 | Anthon |
| 6,061,129 A | 5/2000 | Ershov et al. |
| 6,078,048 A | 6/2000 | Stevens et al. |
| 6,081,331 A | 6/2000 | Teichmann |
| 6,100,974 A | 8/2000 | Reininger |
| 6,119,031 A | 9/2000 | Crowley |
| 6,122,051 A | 9/2000 | Ansley et al. |
| 6,128,078 A | 10/2000 | Fateley |
| 6,151,112 A | 11/2000 | Atkinson et al. |
| 6,166,805 A | 12/2000 | Mori et al. |
| 6,208,413 B1 | 3/2001 | Diehl et al. |
| D441,733 S | 5/2001 | Do et al. |
| 6,238,348 B1 | 5/2001 | Crowley et al. |
| 6,243,170 B1 | 6/2001 | Ershov |
| 6,249,348 B1 | 6/2001 | Jung et al. |
| 6,266,140 B1 | 7/2001 | Xiang et al. |
| 6,288,781 B1 | 9/2001 | Lobb |
| 6,303,934 B1 | 10/2001 | Daly et al. |
| 6,343,227 B1 | 1/2002 | Crowley |
| 6,359,693 B2 | 3/2002 | Smith et al. |
| 6,362,878 B1 | 3/2002 | Wang et al. |
| 6,362,888 B1 | 3/2002 | Jung et al. |
| 6,373,573 B1 | 4/2002 | Jung et al. |
| 6,405,073 B1 | 6/2002 | Crowley et al. |
| 6,411,382 B1 | 6/2002 | Nishina |
| 6,441,900 B1 | 8/2002 | Fujiyoshi |
| 6,452,674 B1 | 9/2002 | Fujiyoshi |
| 6,507,398 B1 | 1/2003 | Arai et al. |
| 6,522,403 B2 | 2/2003 | Wilson et al. |
| 6,538,737 B2 | 3/2003 | Sandstrom et al. |
| 6,549,281 B2 | 4/2003 | Tokumoto |
| 6,574,490 B2 * | 6/2003 | Abbink et al. ............... 600/316 |
| 6,583,873 B1 | 6/2003 | Goncharov et al. |
| 6,587,198 B2 | 7/2003 | Olshausen |
| 6,590,660 B2 | 7/2003 | Jung et al. |
| 6,597,452 B1 | 7/2003 | Jiang et al. |
| 6,606,156 B1 | 8/2003 | Ehbets et al. |
| 6,614,528 B1 | 9/2003 | Bohle |
| 6,630,999 B2 | 10/2003 | Shroder |
| 6,643,011 B2 | 11/2003 | Kojima |
| 6,646,739 B2 | 11/2003 | Kaneko |
| 6,661,513 B1 | 12/2003 | Granger |
| 6,678,044 B2 | 1/2004 | Kaneko |
| 6,683,686 B2 | 1/2004 | Weigold et al. |
| 6,734,966 B2 | 5/2004 | McCarthy |
| 6,741,349 B1 | 5/2004 | Sweatt et al. |
| 6,744,505 B1 | 6/2004 | Wang et al. |
| 6,744,506 B2 | 6/2004 | Kaneko et al. |
| 6,785,002 B2 | 8/2004 | Zarrabian et al. |
| 6,791,086 B2 | 9/2004 | Russell |
| D498,736 S | 11/2004 | Lee |
| 6,823,198 B2 | 11/2004 | Kobayashi |
| D502,159 S | 2/2005 | Chan et al. |
| 6,886,953 B2 | 5/2005 | Cook |
| 6,906,798 B2 | 6/2005 | Kojima et al. |
| 6,917,425 B2 | 7/2005 | Caruso et al. |
| 6,922,240 B2 | 7/2005 | Lerner et al. |
| 6,954,271 B2 | 10/2005 | Curtiss |
| 6,977,727 B2 | 12/2005 | Lerner |
| 6,980,295 B2 | 12/2005 | Lerner |
| 6,985,226 B2 | 1/2006 | Lerner |

| | | |
|---|---|---|
| 6,993,573 B2 | 1/2006 | Hunter |
| 7,003,318 B2 | 2/2006 | Kota et al. |
| 7,006,217 B2 | 2/2006 | Lerner |
| 7,009,702 B2 | 3/2006 | Caruso et al. |
| 7,016,037 B2 | 3/2006 | Chrisp et al. |
| 7,016,038 B2 | 3/2006 | Chrisp et al. |
| 7,019,833 B2 | 3/2006 | Harnisch |
| 7,034,935 B1 | 4/2006 | Kruzelecky |
| D520,976 S | 5/2006 | LaDelfa |
| 7,041,979 B2 | 5/2006 | Chrisp |
| 7,043,284 B2 | 5/2006 | Tornaghi |
| 7,061,611 B2 | 6/2006 | Mitchell |
| 7,075,082 B2 | 7/2006 | Tsao |
| 7,080,912 B2 | 7/2006 | Cook |
| 7,081,955 B2 | 7/2006 | Teichmann et al. |
| D526,983 S | 8/2006 | Gong et al. |
| 7,106,440 B2 | 9/2006 | Granger |
| 7,117,011 B2 | 10/2006 | Makino |
| 7,148,488 B2 | 12/2006 | Horton et al. |
| 7,158,228 B2 | 1/2007 | Psaltis et al. |
| 7,161,673 B2 | 1/2007 | Da Silva |
| 7,164,921 B2 | 1/2007 | Owens et al. |
| 7,170,600 B2 | 1/2007 | Nishii et al. |
| 7,180,590 B2 | 2/2007 | Bastue et al. |
| 7,199,876 B2 | 4/2007 | Mitchell |
| 7,199,877 B2 | 4/2007 | Kehoe et al. |
| 7,228,151 B2 | 6/2007 | Kota et al. |
| 7,233,394 B2 | 6/2007 | Odhner |
| 7,236,243 B2 | 6/2007 | Beecroft et al. |
| 7,239,386 B2 | 7/2007 | Chrisp et al. |
| 7,262,845 B2 | 8/2007 | Avrutsky |
| 7,289,208 B2 | 10/2007 | Vakhshoori et al. |
| 7,304,814 B2 | 12/2007 | Tsao |
| 7,330,258 B2 | 2/2008 | Warren |
| 7,420,663 B2 * | 9/2008 | Wang et al. .................. 356/72 |
| 2001/0048526 A1 | 12/2001 | Bender |
| 2002/0060792 A1 | 5/2002 | Ibsen et al. |
| 2004/0017567 A1 | 1/2004 | Loicht et al. |
| 2004/0057049 A1 | 3/2004 | Bruch et al. |
| 2005/0012927 A1 | 1/2005 | Seyfried et al. |
| 2005/0174573 A1 | 8/2005 | Harvey et al. |
| 2005/0175362 A1 | 8/2005 | Wilson |
| 2006/0082772 A1 | 4/2006 | Kehoe et al. |
| 2006/0139636 A1 | 6/2006 | Kerstan et al. |
| 2006/0166302 A1 * | 7/2006 | Clarke et al. .................. 435/25 |
| 2007/0019194 A1 | 1/2007 | Chen et al. |
| 2007/0030483 A1 | 2/2007 | Everett et al. |
| 2007/0152154 A1 | 7/2007 | DeCamp et al. |
| 2007/0171415 A1 | 7/2007 | Chrisp |
| 2007/0194239 A1 | 8/2007 | McAllister et al. |
| 2007/0211250 A1 | 9/2007 | Teichmann et al. |
| 2007/0236697 A1 | 10/2007 | Zribi et al. |
| 2007/0252989 A1 | 11/2007 | Comstock |
| 2008/0013086 A1 | 1/2008 | Deck |
| 2008/0045825 A1 * | 2/2008 | Melker et al. ................. 600/365 |

FOREIGN PATENT DOCUMENTS

| | | |
|---|---|---|
| JP | A-55-093030 | 7/1980 |
| WO | WO 2004/023974 A2 | 3/2004 |
| WO | WO 2006/102640 A2 | 9/2006 |
| WO | WO 2006/127840 A2 | 11/2006 |

OTHER PUBLICATIONS

Ring, Bell Telephone Laboratories Incorporated, Mobile Telephony—Wide Area Coverage—Case 20564, Dec. 11, 1947, pp. 1-20.
Written Opinion issued in International Application No. PCT/US2008/083613 on Feb. 18, 2009.
International Search Report issued in International Application No. PCT/US2008/083613 on Feb. 18, 2009.
Optical Engineering, Jan./Feb. 1974, vol. 13, No. 1, pp. 25 et seq.
Office Action issued on Jan. 26, 2010 in U.S. Appl. No. 12/149,563.

* cited by examiner

SPECTROMETERS MINIATURIZED FOR WORKING WITH CELLULAR PHONES AND OTHER PORTABLE ELECTRONIC DEVICES

This application claims the benefit of U.S. Provisional Patent Application No. 61/004,959 filed in the U.S. Patent and Trademark Office on Nov. 30, 2007, the entire disclosure of which is hereby incorporated herein by reference in its entirety.

BACKGROUND

1. Field of the Invention

The present invention relates to the domains of optical spectroscopy and cellular phones or other portable electronic devices. In one particular aspect, this invention relates to spectrometers miniaturized for working with cellular phones and other portable electronic devices. In another particular aspect, this invention relates to a cellular phone or other portable electronic device that has a miniaturized spectrometer being built-in or attached.

2. Description of the Related Prior Art, Compact Spectrometers

Instruments used for spectroscopic measurements and applications belong to one family of spectrometers. A spectrometer is an optical instrument for measuring and examining the spectral characteristics of the input light over some portion of the electromagnetic spectrum, where the measured variable is often the light intensity.

A typical optical system of a spectrometer basically comprises an element(s) for collimating, an element(s) for dispersing and an element(s) for focusing to form spectral images. The entrance slit of a spectrometer functions as the input interface, where an optional input optics exists, and divergent input optical beams are fed into the spectrometer. In order to maximize the throughput efficiency, apertures of all optical elements within the spectrometer have to be large enough to accept full optical beams without truncation, which in return, leads to a three-dimensional propagation path. Its detector, usually a (linear) CCD mounted at its spectral image plane, converts optical signals to electronic signals, allowing an instant full spectrum of the input light being acquired since a spectrometer does not have a moving parts for scanning. All of these make a spectrometer, as a useful spectroscopic instrument, cumbersome (i.e. complex in construction), large in body volume and heavy in weight. Moreover, there exist a couple of technical problems inherently associated with this kind of spectrometer: astigmatism over the spectrum on the detector plane, and field curvature from the spectrum focused onto the detector plane, as reviewed by U.S. Pat. No. 5,880,834 (1999) to Chrisp.

As a result, it has become challenge to design and build a spectrometer with innovative features to overcome the drawbacks and technical problems identified above, to which, substantial efforts have been directed and numerous improvements have been published for the purposes of simplifying its optics, minimizing its body volume, reducing its weight, and eliminating optical aberrations, mainly astigmatism and field curvature. Among those areas of concerns, constructing compact spectrometers has generated manifold attentions since the trend in modern spectrometer systems is towards a compact one. A compact spectrometer has the potential to open up for more applications in many industries, as discussed below.

Representatives of the art can be categorized in accordance with their construction features associated with compact spectrometers: spectrometers of simple optics, spectrometers of a monolithic career body, and spectrometer constructed with a waveguide substrate.

A representative of the art for spectrometers of simple optics is U.S. Pat. No. 4,568,187 (1986) to Kita et la, which discloses a compact spectrometer comprising a single concave grating. The concave grating is manufactured with curved grooves of varied spacing for optimum performance, and functions for both dispersing and imaging. It has become a known art that a concave grating sets the minimum number of optical elements needed in a spectrometer, leading to a simplest structure form.

Another representative of the art for spectrometers of simple optics is U.S. Pat. No. 6,606,156 (2003) to Ehbets et la., which discloses a compact spectrometer comprising a concave grating, mounted on one side of the housing. The input port and the detector array are positioned opposite the concave grating, leaving a hollow cavity where the input optical beams propagate.

Another representative of the art for spectrometers of simple optics is U.S. Pat. No. 7,081,955 (2006) to Teichmann et la, which discloses a compact spectrometer comprising two parts: the main body with grating and the focusing element being formed on the top of the housing, and the bottom substrate of detector array with light entrance means. The integrated spectrometer has a hollow cavity where the input optical beams propagate.

Other representatives of the art for spectrometers of simple optics are U.S. Pat. No. 5,424,826 (1995) to Kinney, which discloses an optical micro-spectrometer system, and U.S. Pat. No. 5,550,375 (1996) to Peters et la, which discloses a compact spectrometer designed as infrared spectrometric sensor. Features in common for these two disclosures are that they are constructed for specific applications.

Among the representatives of the art for spectrometers of simple optics, one that has to be referenced is the Japanese Patent Application Publication JP 55-093030 A (1980) to Hasumi Ritsuo, which discloses a cylindrical-lens type spectrometer. Features for this publicized disclosure are that individual cylindrical lenses are used, which manipulate light beams in the vertical and horizontal directions separately, to construct a spectrometer with a compact volume profile.

A representative of the art for spectrometers of a monolithic career body is U.S. Pat. No. 5,026,160 (1991) to Dorain et la, which discloses a such solid monolithic spectrometer that utilizes the Czerny-Turner configuration on a base constructed of BK7 optical glass, to which all components are affixed with optical epoxy, leading to a compact spectrometer with a robust body of thick slab form. Its light entrance means and light detecting means are both placed on the same side of the spectrometer. Another representative of the art for a spectrometer built in a similar approach is disclosed in U.S. Pat. No. 5,754,290 (1998) to Rajic et la, which has an appearance of a solid, rectangular, three-dimensional body of translucent material with defined surfaces.

Another representative of the art for spectrometers of a monolithic career body is U.S. Pat. No. 5,159,404 (1992) to Bittner, which discloses a spectrometer where the concave grating and focusing mirror are combined together on one side of a single glass carrier, and the light entrance means and light detecting means are both placed on the other side of the spectrometer, resulting in a compact spectrometer with a robust body of spherical form.

Another representative of the art for spectrometers of a monolithic career body is U.S. Pat. No. 6,081,331 (2000) to Teichmann, which discloses a spectrometer that utilizes the Fastie-Ebert geometry on a cylinder body of glass, on which a concave mirror surface for collimating and focusing is formed at one end, the light entrance means and light detecting means, as well as the planar reflective grating, are placed on the other end of the career body.

A representative of the art for spectrometers constructed with a waveguide substrate is U.S. Pat. No. 4,744,618 (1988) to Mahlein, which discloses a device designed as multiplexer/demultiplexer for fiber communication systems. It is constructed on a very thin piece of solid monolithic glass. In principle, it works like a compact spectrometer since its input light propagates laterally along the Fastie-Ebert geometry. Meanwhile, its light propagation path is confined vertically based on total internal reflection between two interfaces of glass and the air. A waveguide substrate of sandwich structure is also reported as an alternative embodiment.

There exist a few other representatives of the art for spectrometers constructed with a waveguide substrate, including: U.S. Pat. No. 4,999,489 (1991) to Huggins, and U.S. Pat. No. 5,493,393 (1996) to Beranek et la for optical fiber application. Both of them disclose waveguide based WDM sensing systems. Their optics comprise a thin layer of waveguide as the light propagation media, and a single concave grating formed at the end of the device opposite to the input and output fiber ports.

Another representative of the art for spectrometers constructed with a waveguide substrate is U.S. Pat. No. 4,938,553 (1990) to Maerz et la, which discloses an integrated optical spectrometer having an arrangement of either a film waveguide plus a curved, ribbed waveguide, or only a film waveguide, wherein waveguide structure and ribbed grating are manufactured by etching. The dispersed spectral signals are preferably coupled into output fibers.

Another representative of the art for spectrometers constructed with a waveguide substrate is U.S. Pat. No. 5,812,262 (1998) to Ridyard et la, which discloses a spectrometer for UV radiation, Constructed by a single piece of waveguide carrier, its optics comprises a concave mirror and a reflective planar grating for focusing light from the entrance aperture means onto the radiation detector means. This configuration relies on a fixed order of the optical elements of focusing and then dispersing the light, which makes it difficult to compensate or avoid aberrations.

Another representative of the art for spectrometers constructed with a waveguide substrate is U.S. Pat. No. 7,034,935 (2006) to Kruzelecky, which discloses an infrared spectrometer comprising: a slab waveguide structure having a front input face, a rear concave face, and an output face, a diffraction grating provided on the rear concave face for diffracting the optical signal and directing spectral components onto the output face towards a detector array that is optically coupled to a slab waveguide structure.

As discussed above, most of the related art of compact spectrometers, including those classical spectrometers of simple optics and a monolithic career body, are still considered "cumbersome" and large in volumes for being integrated into a cellular phone to form a standalone system. Exceptions are: (1) the cylindrical-lens type spectrometer, and (2) waveguide based spectrometers, whose volumes are the smallest. Therein the volume difference is caused by the fact that a classical spectrometer is constructed with optical elements of finite two-dimensional apertures and has a light propagation path that is three-dimensional, leading to a larger three-dimensional volume, while in a cylindrical-lens type spectrometer light propagation paths are basically two-dimensional, and for a waveguide based spectrometer it is constructed from a thin monolithic glass substrate where exists a light propagation path in a thin layer (~tens of micrometers) of glass media that are two-dimensional too, or unilateral. A cylindrical-lens type spectrometer or waveguide based technology may be utilized for integrating a compact spectrometer into a cellular phone or other portable electronic device.

However, in practice, there exist other issues that raise extra concerns in consideration of implementing those two candidate techniques. On one hand, a cylindrical-lens type spectrometer comprises more individual optical elements than its existing counterparts, leading to increases in both manufacturing cost and volume of the integrated package. On the other hand, the manufacturing process of waveguide products is expensive, and there are other technical concerned drawbacks associated with waveguide performance, including high propagation loss, stray light caused by scattering at waveguide boundary, etc . . . Besides, coupling efficiency of waveguide devices are very susceptible to misalignment at input ends. All of these factors have negative implications when considering whether to apply waveguide based spectrometers in more applications.

In general, existing spectrometers have not been an object of miniaturization as has been other technological machines and equipment because of the lack of technology in making it so. Thus, wider applications of spectrometers have not been possible for areas where miniaturization has become increasingly necessary or preferable. These disadvantages of existing spectrometers have been overcome with the present invention, both in the invention itself and the method with which it is made.

3. Description of the Related Prior Art, Cellular Phone

A cellular phone is a wireless and mobile phone. For the simplicity of discussion in the following sections, the term "cellular phone" and "mobile phone" are used equally in an exchangeable way. The earliest representative of the art of wireless telephone is U.S. Pat. No. 887,357 (1908) to Stubblefield, which discloses an invention applied to "cave radio" telephones between a vehicle to a vehicle, and a vehicle to a station. Since then, radiophones have gone through a long and varied history.

The introduction of cells for mobile phone base stations was invented in 1947 by Bell Labs engineers at AT&T. Memo by Douglas H. Ring proposing hexagonal cells, Nov. 11, 1947, Bell Telephone Laborlatries Incorporated. One of representatives for practically implementing cellular phone technology is U.S. Pat. No. 3,663,762 (1972) to Joel, Jr., which discloses an automatic "call handoff" system to allow mobile phones to move through several cell areas during a single conversation without loss of conversation. In general, Motorola is widely considered to be the inventor of the first practical mobile phone for handheld use in a non-vehicle setting. A representative of the art of cellular phone from Motorola is U.S. Pat. No. 3,906,166 (1975) to Cooper et la, a Motorola manager who made the first call on a handheld mobile phone on Apr. 3, 1973.

Other representatives of the art of historical significance include: U.S. Pat. No. 4,399,555 (1983) to MacDonald et la, U.S. Pat. No. 5,265,158 (1993) to Tattari, U.S. Pat. No. 5,722,067 (1998) to Fougnies, and U.S. Pat. No. 5,841,856 (1998) to Yoshiyuki Ide. Throughout the period covered by these representatives listed above, cellular phones are commercially introduced to civilians through three generations: 1G (1980~1990) of an analog signal transmission technique supporting basic voice communication only, 2G (1990~2000) of digital signal transmission technique, and 3G (2000~2007) that offers increasing wideband transmission capability.

As technologies applied to cellular phone advance, more new features are being incorporated into cellular phones, resulting in new types of cellular phones being introduced with different names, like camera phones, PDA (personal digital assistant) phone or smartphone, and GPS phone, etc.

A camera phone is a mobile phone that has a camera built-in and is coupled with a server-based infrastructure or protocol, which allows the user to instantly share pictures and video with someone that has a device adapted to receive pictures and video. A representative of the art of camera phone is U.S. Pat. No. D405,457 (1999) to Kawashima, which discloses an ornamental design for a digital camera with cellular phone. Other typical representatives of the art of camera phone include: U.S. Pat. No. 6,823,198 (2004) to Kobayashi, U.S. Pat. No. 7,003,318 (2006) to Kota, et al, U.S. Pat. No. 7,117,011 (2006) to Makino, and U.S. Pat. No. 7,228,151 (2007) to Kota, et al, etc.

A PDA phone is a PDA and cell phone combination. PDA phones predominantly have data capabilities, multiple data input methods, wireless email functions, security and device management features, organizer functions, USB connection, charging from PC and extensive third party application support, supported by window based operating system. A smartphone on the other hand, is mainly a phone with some PDA phone features like organizer function, data viewing capabilities without editing functions. A representative of the art of PDA phone is U.S. Pat. No. D441,733 (2001) to Do, et al., which discloses a ornamental design for a multiple wireless PDA phone. There exist a few other representatives of the art of PDA phone, including U.S. Pat. No. D498,736 (2004) to Lee, U.S. Pat. No. D502,159 (2005) to Chan, et al., U.S. Pat. No. 7,043,284 (2006) to Tornaghi, U.S. Pat. No. D520,976 (2006) to LaDelfa, and U.S. Pat. No. D526,983 (2006) to Gong, et al.

Another representative of the art of cellular phone is: U.S. Pat. No. 6,993,573 (2006) Hunter, which discloses a camera cellular phone that is adapted to image a machine-readable code such as a bar code. It decodes the bar code and sends the bar code data over the Internet to a resolution server that will return an associated URL that will link the camera phone to content on an information server.

Another representative of the art of cellular phone is: U.S. Pat. No. 7,164,921 (2007) Owens, et al, which discloses a mobile phone having an internal GPS-receiver. It accommodates any applications in which a wireless communications device such as a cell phone can be caused to report location, with the phone initially in an off condition, From above reviews of related prior art, it can be seen that a cellular phone has become so powerful that it have a numerous advanced capabilities, including: onboard CPU for data processing, LCD for real-time display, USB port for connection, operating system for supporting working environment, and the wireless communication capability to connect to other cellular phones or onto the internet. All of these considerations make a cellular phone an ideal platform for supporting real-time applications associated with a spectrometer.

On the other hand, it will not be physically possible to integrate a spectrometer into or with a cellular phone together, unless a spectrometer's size/volume is significantly reduced with a footprint compatible to that of a cellular phone. Thus, it is the intention of this invention to provide compact spectrometers miniaturized for working with cellular phones or other portable electronic device without scarifying their performances.

SUMMARY

Definition and Explanation of the Coordinate System:

A Cartesian co-ordinate system denoted by XYZO is to be referenced in the discussions to follow, where the optical system of a spectrometer resides and light propagates. The co-ordinate system has three axes: X, Y, Z and an origin O. Two important planes are defined here: XOZ represents the horizontal plane, or the sagittal plane; YOZ represents the vertical plane, or the tangential plane. Z represents the propagation direction of light. A beam of light is considered to have a three-dimensional path, if it converges, or diverges, or maintains a finite collimated size in both the tangential and sagittal planes as it propagates in Z direction. A beam of light is considered having a substantially two-dimensional (substantially unilateralized) path, if it converges, or diverges, or maintains a finite collimated size in either the tangential or the sagittal planes, but is confined within a thin layer in or parallel to the other plane, as it propagates in Z direction.

The main object of the embodiments is to provide an optical technique that makes the propagation path, either in transparent media or in free space, of the optical beams emitting from a small input aperture/slit of a spectrometer, substantially two-dimensional or substantially unilateralized, enabling physical sizes of any optical elements needed thereafter to construct a spectrometer being reduced significantly in one dimension. As a result, a significant reduction of device volume will be achieved, which is applicable and beneficial to a compact spectrometer, and thus such a compact spectrometer can be integrated into a cellular phone or other portable electronic device.

The above description sets forth, rather broadly, a summary of the present invention so that the detailed description that follows may be better understood and contributions of the present invention to the art may be better appreciated. Some of the embodiments to follow of the present invention may not include all of the features or characteristics listed in the above summary. There are, of course, additional features of the invention that will be described below and will form the subject matter of claims. In this respect, before explaining any embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

In one aspect, it is an object of the present invention to provide a means to manipulate the propagation properties of the optical beams separately in two independent directions, i.e. in the tangential plane and the sagittal plane, at any intersecting locations between optical beams and optical elements/surfaces inside a spectrometer. The said means calls for usage of optical elements, which have cylindrical or toroidal surfaces with main optical powers only in one direction, i.e. either in the tangential plane or in the sagittal plane. The said optical elements include all types of cylindrical and toroidal lenses; all types of cylindrical and toroidal mirrors; one-dimensional, reflective gratings of planar, or concave cylindrical substrates; herein "all types" represents properties of positive and negative optical power, spherical and aspherical shapes for cross-section.

One aspect of the present invention is to provide an entrance aperture of small size at the entrance slit position of spectrometers, where the said entrance aperture can be the core of a single mode fiber, or the core of a multi-mode fiber, or pinholes of diameters similar to those of fibers' cores, or a slit of fiber core widths whose preferred height is less than a few millimeters. The optical outputs of the said entrance aperture may have symmetrical or asymmetrical cone shapes, whose propagation paths are three-dimensional.

Another aspect of the present invention is to provide a collimating means to collimate the optical beams emitting from the said entrance aperture in the tangential plane only, making the output beams of the said collimating means anamorphic, which is substantially collimated in the tangential plane, but propagates in divergence freely in the sagittal plane. The said collimating means can be a cylindrical or toroidal lens, or a concave cylindrical or toroidal mirror, or a concave conic cylindrical or toroidal mirror, all of which have main optical power in the tangential plane, but have no or little optical power in the sagittal plane. The said collimating means is properly positioned behind the entrance aperture in the optical train of the spectrometer's optics, closely enough that its outputs of partially collimated anamorphic beams maintain a small and finite collimated size (no more than a few millimeters) in the tangential plane, whose propagation paths are substantially two-dimensional.

Another aspect of the present invention is to provide a dispersing-focusing means, which resides at certain distance behind the collimating means in the optical train of the spectrometer's optics. The said dispersing-focusing means is capable of performing two tasks in the sagittal plane only: (1) dispersing the input optical beams received from the said collimating means; (2) forming spectral images of the said entrance aperture onto a detector surface. The said dispersing-focusing means can be any one of that of embodiments to be explained below. The outputs of the said dispersing-focusing means remain partially collimated with a small and finite collimated size in the tangential plane, but are focused into spectral images at the said detector surface in the sagittal plane. The said outputs have propagation paths that are substantially two-dimensional.

Another aspect of the present invention is to provide a focusing means to focus the optical beams received from the said dispersing-focusing means onto the said detector surface in the tangential plane only. The said focusing means can be a cylindrical or toroidal lens, or a concave cylindrical or toroidal mirror, or a concave conic cylindrical or toroidal mirror, all of which have main optical power in the tangential plane, but have no or little optical power in the sagittal plane. As a result, the output of the said focusing means form a linear spectral image at the said detector surface. The said detector is a linear array of detector pixels residing behind the said focusing means, at the end of the optical train of the spectrometer's optics.

One embodiment of the present invention is directed to a spectrometer comprising: (1) the said entrance aperture, (2) the said collimating means, the said dispersing-focusing means, (6) the said focusing means and (7) the said detector, where the said dispersing-focusing means is a reflectance sub-system comprising: (3) a cylindrical/toroidal mirror for collimating in the sagittal plane, (4) a reflective grating for dispersing in the sagittal plane and (5) a cylindrical/toroidal mirror for focusing in the sagittal plane. Optical means from (2) to (6) can be fabricated by a thin piece of monolithic transparent material. The propagation paths within the spectrometer from (1) to (7) are substantially two-dimensional.

Another embodiment of the present invention is directed to a spectrometer with Fastie-Ebert configuration comprising: (1) the said entrance aperture, (2) the said collimating means, the said dispersing-focusing means, (5) the said focusing means and (6) the said detector, where the said dispersing-focusing means is a reflectance sub-system comprising: (3) a cylindrical/toroidal mirror for both collimating and focusing in the sagittal plane, and (4) a reflective grating for dispersing in the sagittal plane. Optical means from (2) to (5) can be fabricated by a thin piece of monolithic transparent material. The propagation paths within the spectrometer from (1) to (6) are substantially two-dimensional.

Another embodiment of the present invention is directed to a spectrometer with Czerny-Turner configuration comprising: (1) the said entrance aperture, (2) the said collimating means, the said dispersing-focusing means, (6) the said focusing means and (7) the said detector, where the said dispersing-focusing means is a reflectance sub-system comprising: (3) a cylindrical/toroidal mirror for collimating in the sagittal plane, (4) a reflective grating for dispersing in the sagittal plane and (5) a cylindrical/toroidal mirror for focusing in the sagittal plane. Optical means from (2) to (6) can be fabricated by a thin piece of monolithic transparent material. The propagation paths within the spectrometer from (1) to (7) are substantially two-dimensional.

Another embodiment of the present invention is directed to a spectrometer comprising (1) the said entrance aperture, (2) the said collimating means, the said dispersing-focusing means, (5) the said focusing means and (6) the said detector, wherein the said dispersing-focusing means is a hybrid sub-system comprising: (3) a cylindrical/toroidal lens for collimating and focusing in the sagittal plane, and (4) a reflective grating for dispersing in the sagittal plane. The propagation paths within the spectrometer from (1) to (6) are substantially two-dimensional.

Another embodiment of the present invention is directed to a spectrometer comprising: (1) the said entrance aperture, (2) the said collimating means, (3) the said dispersing-focusing means, (4) the said focusing means and (5) the said detector, where the said dispersing-focusing means is a concave (cylindrical or toroidal) reflective grating for dispersing and focusing in the sagittal plane. Optical means from (2) to (4) can be fabricated by a thin piece of monolithic transparent material. The propagation paths within the spectrometer from (1) to (5) are substantially two-dimensional.

One important aspect of the present invention is directed to build a spectrometer based on one of above embodiments or their modified configurations, in which the said collimating means and the said focusing means fulfill tasks of (1) generating images of the said entrance aperture onto the said detector surface in the tangential plane, and (2) making the propagation paths of optical beams within the spectrometer substantially two-dimensional. Meanwhile, the said dispersing-focusing means of the said spectrometer fulfills tasks of (i) dispersing the received optical beams into spectra in the sagittal plane, and (ii) generating spectral images of the said entrance aperture onto the said detector surface in the sagittal plane. In this way, significant improvements are achieved in two aspect: (a) sizes and dimensions of all optical elements used inside the said spectrometer are significantly reduced in Y direction, i.e. in the vertical plane or the tangential plane; as a result, the instrument/device volume is significantly reduce; (b) optical aberration of astigmatism and curvature of spectral images are well compensated.

It is an object of the present invention to physically integrate a compact spectrometer, preferably based on one of those embodiments specified above, into a cellular phone, or other portable electronic device, to form a standalone system for spectroscopic applications. Such a combined system will take optical inputs, through an optical fiber or direct coupling optics via the entrance aperture, into its built-in spectrometer for spectral measurements. The cellular phone or other portable electronic device is able to process the data, or display measurement results, or send the measurement data to a remote receiver via wireless communication.

It is another object of the present invention to physically attach a compact spectrometer, preferably based on one of those embodiments specified above, to a cellular phone to form a standalone system for spectroscopic applications. The said spectrometer is electronically linked with the cellular phone or other portable electronic device via USB connections. Such a combined system will take optical inputs, through an optical fiber or direct coupling optics via the entrance aperture, into the attached spectrometer for spectral measurements. The cellular phone is able to process the data, or display measurement results, or send the measurement data to a remote receiver via wireless communication.

It is another object of the present invention to physically integrate or attach a compact spectrometer, which is built with a monolithic substrate based on waveguide technology, to a cellular phone or other electronic device to form a standalone system for spectroscopic applications. The said spectrometer comprise: (1) the entrance aperture, (2) the optical coupling means, (3) the said dispersing-focusing means, and (4) the said detector, wherein the said dispersing-focusing means is fabricated on a thin piece of monolithic transparent waveguide substrate, whose optics comprise one of the following approaches: optics of a concave mirror, reflective grating and another concave mirror; optics of Czerny-Turner configuration; optics of Fastie-Ebert configuration; or optics of a concave reflective grating. The propagation paths of (3) within the spectrometer are substantially two-dimensional. Using the combined system, the cellular phone or other portable electronic device is able to process the data, or display measurement results, or send the measurement data to a remote receiver via wireless communication.

It is another objective to use the said standalone system mentioned above, i.e. "spectrometer phone", with a laser as a Raman spectrometer system. Such a portable Raman system can be used to identify materials in many applications. One example is that it makes it possible for civilians to fulfill daily routine health monitoring easily, for example, non-invasive blood glucose monitoring by diabetes patients at home, or non-invasive blood cholesterols' monitoring by a user.

It is another objective to use the said standalone system mentioned above, i.e. "spectrometer phone", with a NIR source as a NIR spectrometer system. Such a portable NIR system can be used to identify materials in many applications. One example is that it makes it possible for civilians to fulfill daily routine health monitoring easily, for example, non-invasive blood glucose monitoring by diabetes patients at home, or non-invasive blood cholesterols' monitoring by a user.

It is another objective to use the said standalone system mentioned above, i.e. "spectrometer phone", to measure colors or spectra of input light signals over at least one of the spectral bands: ultra-violet, visible, near infrared and infrared. The said input light signals fall into at least one kind of electro-magnetic waves: radiating from a source, reflected from an object or materials, transmitting through an object or materials, excited fluorescent radiation by a UV light or a laser from an object or materials, or excited Raman radiation by a laser from an object or materials.

The above summary of the present invention is not intended to describe each illustrated embodiment or every implementation of the present invention. The figures and the detailed description, which follow more particularly, exemplify these embodiments.

BRIEF DESCRIPTION OF THE DRAWINGS

FIG. 1(a) represents a prior art, and FIGS. 1(b), (c) and (d) represent three preferred embodiments of the same spectrometer based on the present invention.

FIG. 2(a) represents a prior art, and FIG. 2(b) represents one embodiment of the same spectrometer based on the present invention.

FIG. 3(a) represents a prior art, and FIG. 3(b) represents one embodiment of the same spectrometer based on the present invention.

FIG. 4(a) represents a prior art, and FIG. 4(b) represents one embodiment of the same spectrometer based on the present invention.

DETAILED DESCRIPTION OF EMBODIMENTS

Figure 1:
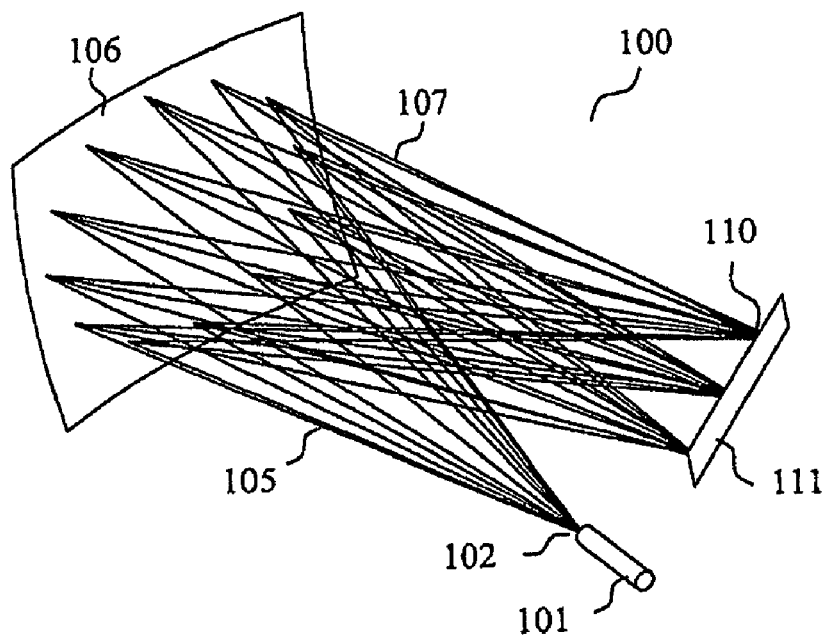
FIG. 1 shows perspective views of a compact spectrometer comprising a concave grating only, where
Figure 1:
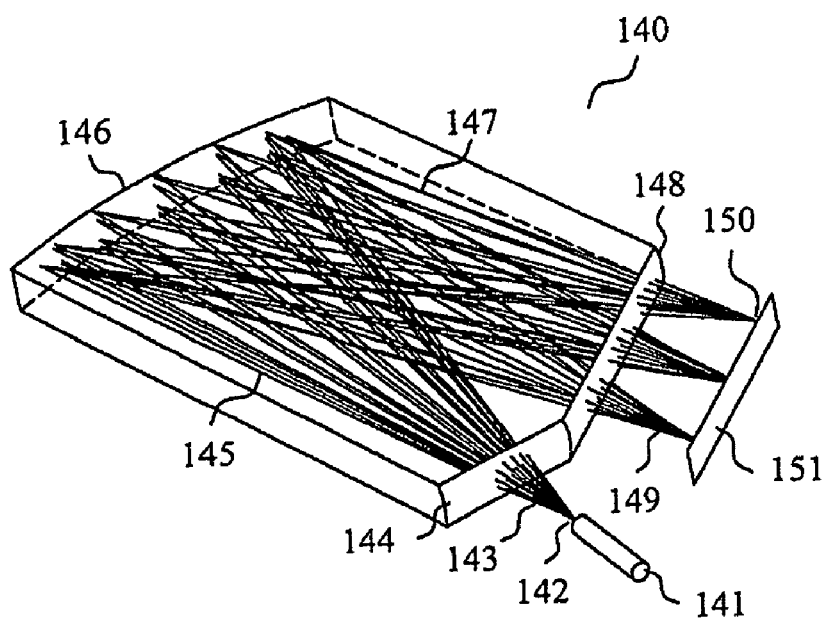
Figure 1:
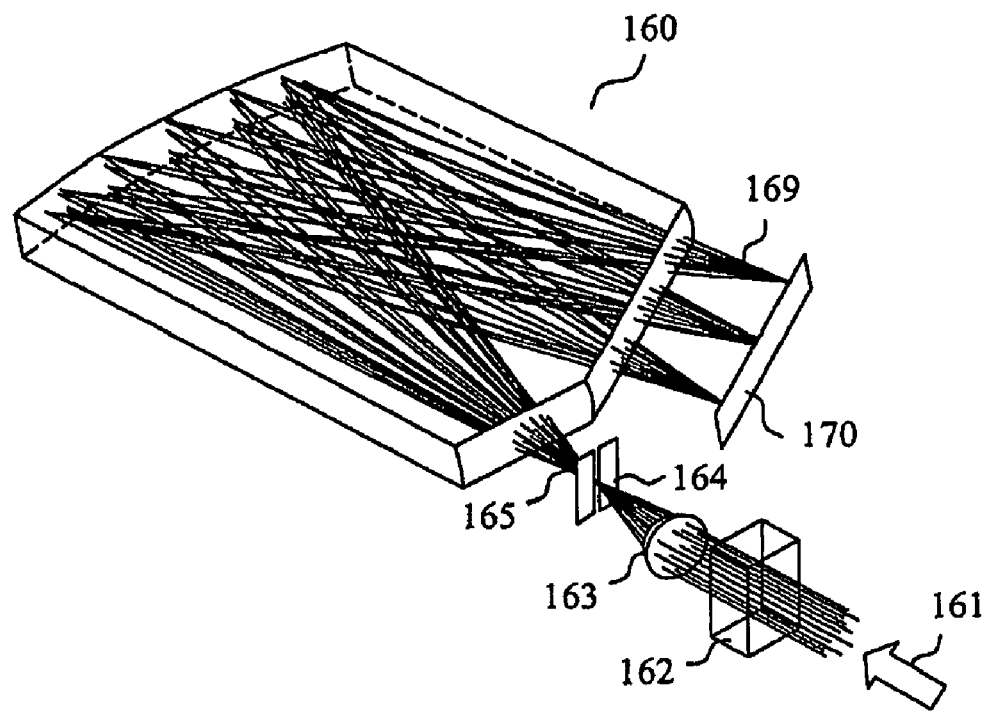
Figure 1:
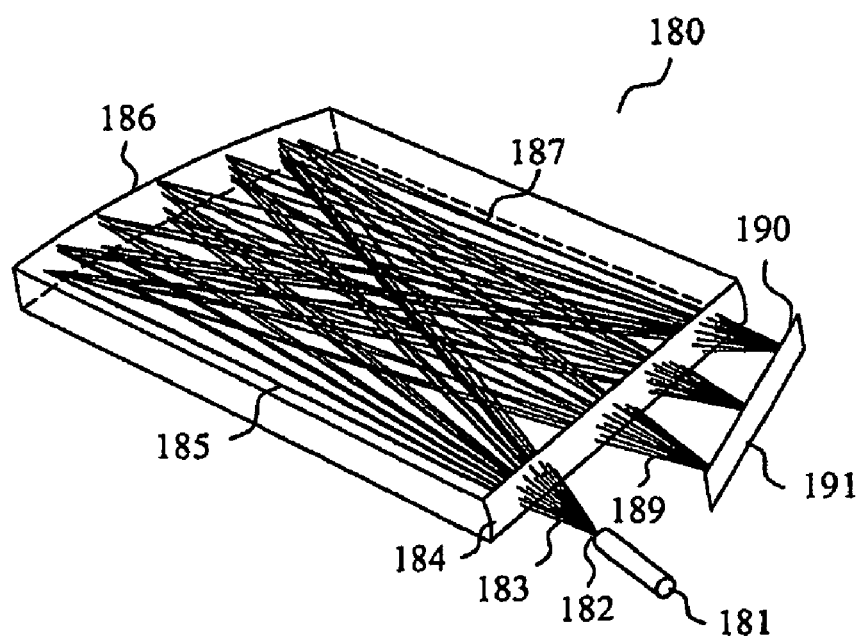

Referring now to the drawings, to the following detailed description, and to the incorporated materials, detailed information about the invention is provided including the description of specific embodiments. The detailed description serves to explain the principles of the invention. The invention is susceptible to modifications and alternative forms. The invention is not limited to the particular forms and embodiments disclosed. The invention covers all modifications, equivalents, and alternatives falling within the spirit and scope of the invention as defined by the claims.

Referring to FIG. 1(a), a prior art of a compact spectrometer is illustrated in ray-trace form, which is designated by the general reference numeral 100. Its optics comprises an entrance aperture 102 that is the core of the optical fiber 101 for input signal delivery, and a concave diffraction grating 106. For the spectrometer 100, the input light 105 emits from the entrance aperture 102 and propagates in divergence towards the concave grating 106, which disperses, in a reflective manner, the divergent light 105 and focuses it into the convergent light 107 to form spectral images 110 on the detector 111. As shown in FIG. 1(a), the propagation paths for the divergent light 105 and the convergent light 107 are all three-dimensional. The single key optical element within the spectrometer 100, i.e. the concave grating 106, must have finite working apertures large enough to accept and manipulate the light 105 and 107 without truncating them at any locations. As a result, the overall dimensional volume necessitated to construct the spectrometer 100 is three-dimensional, which is too large for being integrated into a cellular phone package, or other portable electronic device package, and very difficult or impossible to be reduced without sacrificing its performance characteristics.

In FIG. 1(b), one preferred embodiment of the same compact spectrometer as shown in FIG. 1(a) in ray-trace form is illustrated based on the present invention, which is designated by the general reference numeral 140. The spectrometer 140 is constructed by combining its three key optical elements together with a single piece of monolithic transparent carrier. Its optics comprises an entrance aperture 142 that is the core of the optical fiber 141 for input signal delivery, a first cylindrical surface 144, a concave cylindrical grating 146, and a second cylindrical surface 148. For the spectrometer 140, the input light 143 emits from the entrance aperture 142 and propagates in divergence over a very short distance, then is intercepted by the first cylindrical surface 144, which collimates the divergent light 143 only in the tangential plane, converting it into a partially collimated light, i.e. the anamorphic light 145, which is collimated in the tangential plane, but remains divergent in the sagittal plane. The light 145 propagates in the transparent medium and is intercepted by the concave cylindrical grating 146, which disperses, in a reflective manner, the light 145 and focuses it only in the sagittal plane into the anamorphic light 147, which remains collimated in the tangential plane, but is dispersed and convergent in the sagittal plane. Upon being intercepted by the second cylindrical surface 148, the light 147 is focused in the tangential plane into the fully convergent light 149 to form spectral images 150 on the detector 151. As shown in FIG. 1(b), the propagation paths for the anamorphic light 145 and the anamorphic light 147 are all substantially two-dimensional. The three key optical surfaces within the spectrometer 140, i.e. the first cylindrical surface 144, the concave cylindrical grating 146 and the second cylindrical surface 148, must have finite working aperture dimensions large enough only in the sagittal direction (horizontal), but very small aperture dimensions needed in the tangential direction (vertical), in order to accept and manipulate light 143, 145, 147 and 149 without truncating them at any locations. In practice, the tangential dimensions (vertical) of those key optical surfaces needed become a small fractions of their original values in the same prior art, for example, around 1/5~1/10 (i.e., an approximate reduction in size of 80% to 90% may be achieved) or even better. As a result, the overall dimensional volume necessitated to construct the spectrometer 140 is substantially two-dimensional, or substantially unilateral, which is significantly reduced compared with that of its prior art spectrometer without sacrificing its performance characteristics. Thus it is possible, based on the present invention, to easily construct a spectrometer fabricated with a single piece of thin transparent carrier, which is robust and of very compact volume, and can be integrated into a cellular phone package, or other portable electronic device, to form a complete standalone spectroscopic system for many application, for example, real-time spectroscopic measurements.

In FIG. 1(c), another embodiment of the same compact spectrometer as shown in FIG. 1(b) in ray-trace form is illustrated based on the present invention, which is designated by the general reference numeral 160. It only differentiates from 140 of FIG. 1(b) by its input coupling optics, where the illuminating light 161 transmits through the object or material under test 162, and is then focused by the input coupling lens 163 onto the input aperture, here a slit 164. After propagating through the slit 164, the input light 165 enters the spectrometer 160, which forms spectral images 169 on the detector 170.

In FIG. 1(d), another embodiment of the same compact spectrometer as shown in FIGS. 1(a) and (b) in ray-trace form is illustrated based on the present invention, which is designated by the general reference numeral 180. It is similar to that of the embodiment of FIG. 1(b) with even simpler structure: the two cylindrical surfaces 144 and 148 of spectrometer 140 in FIG. 1(b) are combined into a single cylindrical surface 184 of spectrometer 180 in FIG. 1(d). Similarly, this spectrometer is also robust and of very compact volume, and can be integrated into a cellular phone package, or other portable electronic device package, to form a complete standalone spectroscopic system for many application, for example, real-time spectroscopic measurements.

Figure 2:
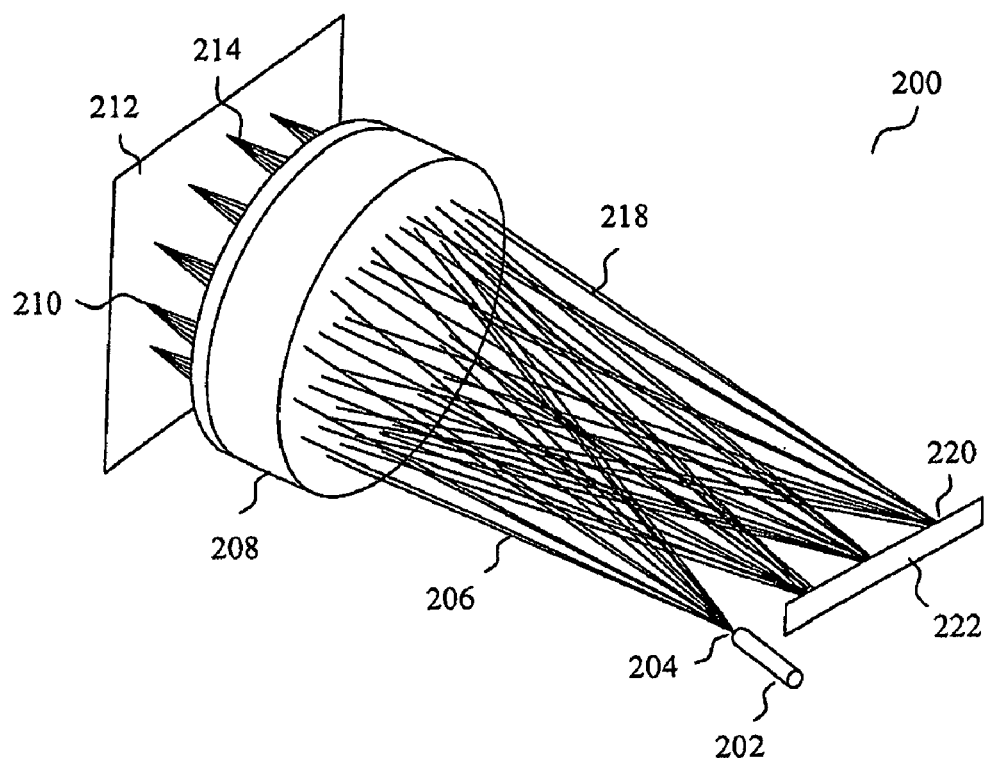
FIG. 2 shows perspective views of a compact spectrometer comprising a lens and a reflective grating, where
Figure 2:
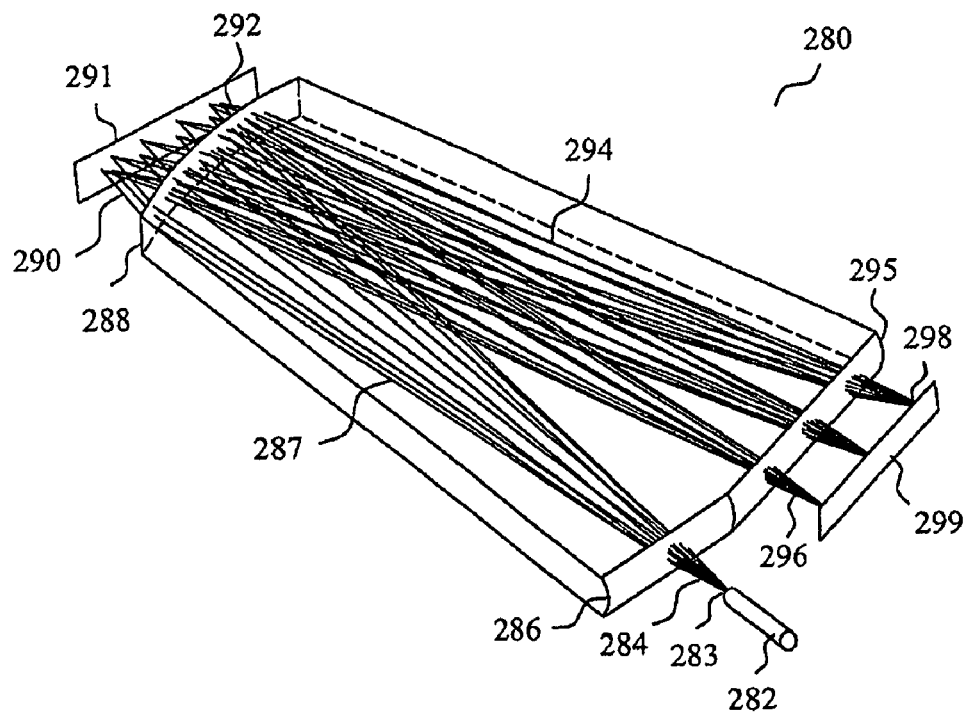

Next referring to FIG. 2(a), a prior art of a compact spectrometer is illustrated in ray-trace form, which is designated by the general reference numeral 200. Its optics comprises an entrance aperture 204 that is the core of the optical fiber 202 for input signal delivery, a lens 208 for both collimating and focusing, and a reflective diffraction grating 212. For the spectrometer 200, the input light 206 emits from the entrance aperture 204 and propagates in divergence towards the lens 208, which collimates the divergent light 206 into the collimated light 210. The collimated light 210 propagates and is incident upon the grating 212, which disperses, in a reflective manner, the light 210 into the dispersive collimated light 214, and then the same lens 208 focuses the light 214 into the convergent light 218 to form spectral images 220 on the detector 222. As shown in FIG. 2(a), the propagation paths for the divergent light 206, the collimated light 210, the dispersive light 214, and the convergent light 218 are all three-dimensional. The two key optical elements within the spectrometer 200, i.e. the lens 208 and the grating 212, must have finite working apertures large enough to accept and manipulate the light 206, 210, 214 and 218 without truncating them at any locations. As a result, the overall dimensional volume necessitated to construct the spectrometer 200 is three-dimensional, which is too large for being integrated into a cellular phone package, or other portable electronic device, and very difficult or impossible to be reduced without sacrificing its performance characteristics.

In FIG. 2(b), one embodiment of the same compact spectrometer as shown in FIG. 2(a) is illustrated in ray-trace form based on the present invention, which is designated by the general reference numeral 280. The spectrometer 280 is constructed by combining its three key optical surfaces necessitated to build a compact spectrometer together with a single piece of monolithic transparent carrier. Its optics comprises an entrance aperture 283 that is the core of the optical fiber 282 for input signal delivery, a first cylindrical surface 286, a second cylindrical surface 288, a reflective diffraction grating 291 and a third cylindrical surface 295. For the spectrometer 280, the input light 284 emits from the entrance aperture 283 and propagates in divergence over a very short distance, then is intercepted by the first cylindrical surface 286, which collimates the divergent light 284 only in the tangential plane, converting it into a partially collimated light, i.e. the anamorphic light 287, which is collimated in the tangential plane, but remains divergent in the sagittal plane. The light 287 propagates and is intercepted by the second cylindrical surface 288, which collimates it only in the sagittal plane, converting it into the fully collimated light 290. The light 290 continues to propagate and is incident upon the grating 291, which disperses, in a reflective manner, the light 290 into dispersive collimated light 292. Upon being intercepted by the same cylindrical surface 288, the light 292 is partially focused in the sagittal plane into the light 294, which is further partially focused by the third cylindrical surface 295 in the tangential plane into the fully convergent light 296 to form spectral images 298 on the detector 299. As shown in FIG. 2(b), the propagation paths for the anamorphic light 287, collimated light 290, dispersive light 292, and the anamorphic light 294 are all substantially two-dimensional. The four key optical elements/surfaces within the spectrometer 280, i.e. the first cylindrical surface 286, the second cylindrical surface 288, the grating 291 and the third cylindrical surface 295, must have finite working aperture dimensions large enough only in the sagittal direction (horizontal), but very small aperture dimensions needed in the tangential direction (vertical), in order to accept and manipulate light 284, 287, 290, 292, 294 and 296 without truncating them at any locations. In practice, the tangential dimensions (vertical) of those key optical surfaces needed become a small fractions of their original values in the same prior art, for example, around $1/5 \sim 1/10$ (i.e., an approximate reduction in size of 80% to 90% may be achieved) or even better. As a result, the overall dimensional volume necessitated to construct the spectrometer 280 is two-dimensional, or unilateral, which is significantly reduced compared with that of its prior art spectrometer without sacrificing its performance characteristics. Thus it is possible, based on the present invention, to easily construct a spectrometer fabricated with a single piece of thin transparent carrier, which is robust and of very compact volume, and can be integrated into a cellular phone package, or other portable electronic device package, to form a complete standalone spectroscopic system for many application, for example, real-time spectroscopic measurements.

Figure 3:
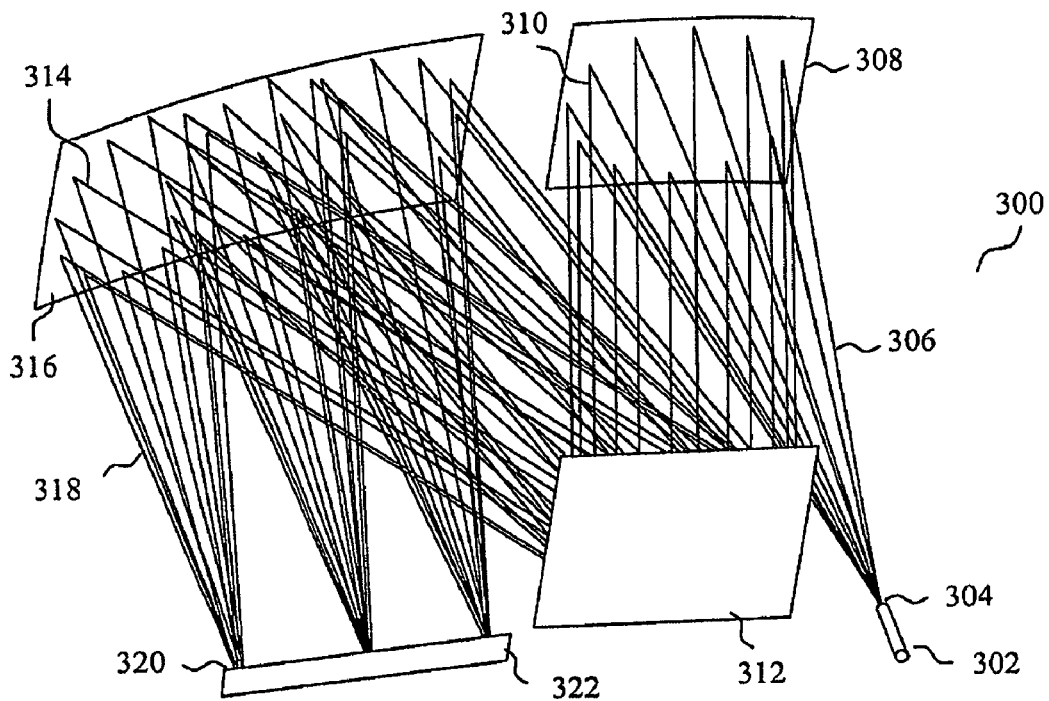
FIG. 3 shows perspective views of a mirror spectrometer of Czerny-Turner or Fastie-Ebert configuration, where
Figure 3:
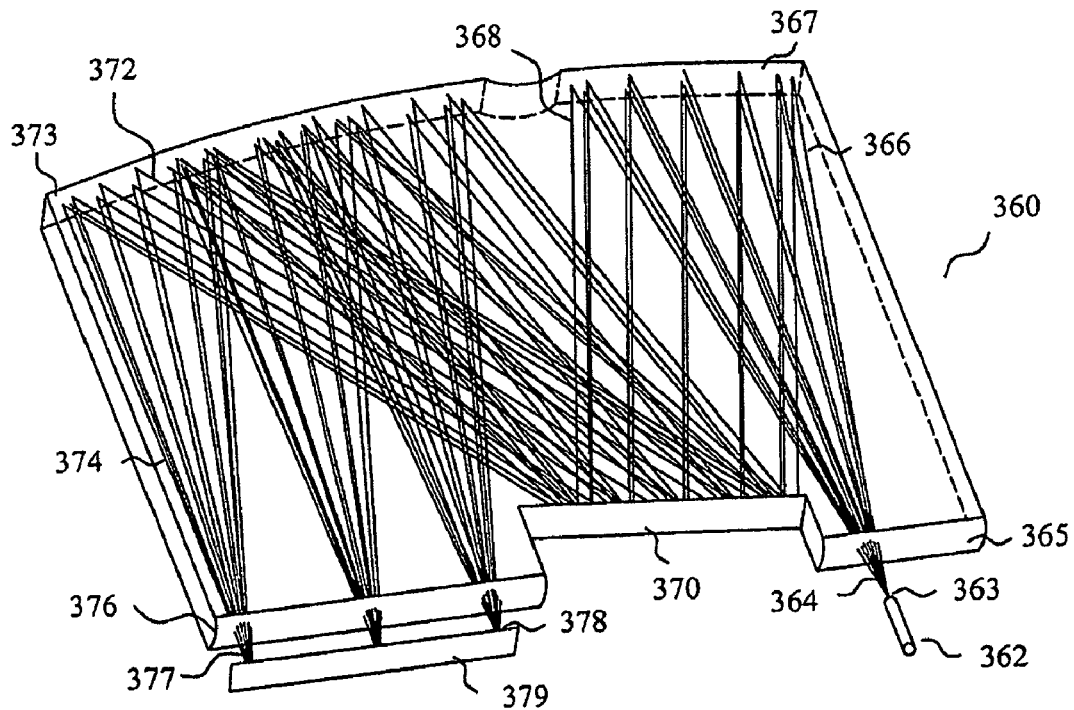

Next, referring to FIG. 3(a), a prior art of a mirror spectrometer of Czerny-Turner geometry is illustrated in ray-trace form, which is designated by the general reference numeral 300. Its optics comprises an entrance aperture 304 that is the core of the optical fiber 302 for input signal delivery, a collimating mirror 308, a reflective diffraction grating 312 and a focusing mirror 316 (its optics becomes a Fastie-Ebert geometry when mirror 308 and mirror 316 are two areas of the same single mirror). For the spectrometer 300, the input light 306 emits from the entrance aperture 304 and propagates in divergence towards the collimating mirror 308, which collimates the divergent light 306 into the collimated light 310. The collimated light 310 propagates and is incident upon the grating 312, which disperses, in a reflective manner, the light 310 into the dispersive collimated light 314, and then the focusing mirror 316 focuses the light 314 into the convergent light 318 to form spectral images 320 on the detector 322. As shown in FIG. 3(a), the propagation paths for the divergent light 306, the collimated light 310, the dispersive light 314, and the convergent light 318 are all three-dimensional. The three key optical elements within the spectrometer 300, i.e. the collimating mirror 308, the grating 312 and the focusing mirror 316, must have finite working apertures large enough to accept and manipulate the light 306, 310, 314 and 318 without truncating them at any locations. As a result, the overall dimensional volume necessitated to construct the spectrometer 300 is three-dimensional, which is too large for being integrated into a cellular phone package, and very difficult or impossible to be reduced without sacrificing its performance characteristics.

In FIG. 3(b), one embodiment of the same mirror spectrometer of Czerny-Turner geometry as shown in FIG. 3(a) is illustrated in ray-trace form based on the present invention, which is designated by the general reference numeral 360. The spectrometer 360 is constructed by combining the five key optical surfaces necessitated to build a compact spectrometer together with a single piece of monolithic transparent carrier. Its optics comprises an entrance aperture 363 that is the core of the optical fiber 362 for input signal delivery, a first cylindrical surface 365, a first cylindrical mirror 367, a reflective diffraction grating 370, a second cylindrical mirror 373 and a second cylindrical surface 376. For the spectrometer 360, the input light 364 emits from the entrance aperture 363 and propagates in divergence over a very short distance, then is intercepted by the first cylindrical surface 365, which collimates the divergent light 364 only in the tangential plane, converting it into a partially collimated light, i.e. the anamorphic light 366, which is collimated in the tangential plane, but remains divergent in the sagittal plane. The light 366 propagates and is intercepted by the first cylindrical mirror 367, which collimates it only in the sagittal plane, converting it into the fully collimated light 368. The light 368 continues to propagate and is incident upon the grating 370, which disperses, in a reflective manner, the light 368 into the dispersive collimated light 372. Upon being intercepted by the second cylindrical mirror 373, the light 372 is partially focused in the sagittal plane into the light 374, which is further partially focused by the second cylindrical surface 376 in the tangential plane into the fully convergent light 377 to form spectral images 378 on the detector 379. As shown in FIG. 3(b), the propagation paths for the anamorphic light 366, the collimated light 368, the dispersive light 372, and the anamorphic light 374 are all substantially two-dimensional. The five key optical surfaces within the spectrometer 360, i.e. the first cylindrical surface 365, the first cylindrical mirror 367, the grating 370, the second cylindrical mirror 373 and the second cylindrical surface 376, must have finite working aperture dimensions large enough only in the sagittal direction (horizontal), but very small aperture dimensions needed in the tangential direction (vertical), in order to accept and manipulate light 364, 366, 368, 372, 374 and 377 without truncating them at any locations. In practice, the tangential dimensions (vertical) of those key optical surfaces needed become a small fractions of their original values in the same prior art, for example, around $1/5 \sim 1/10$ (i.e., an approximate reduction in size of 80% to 90% may be achieved) or even better. As a result, the overall dimensional volume necessitated to construct the spectrometer 360 is substantially two-dimensional, or substantially unilateral, which is significantly reduced compared with that of its prior art spectrometer without sacrificing its performance characteristics. Thus it is possible, based on the present invention, to easily construct a spectrometer fabricated with a single piece of thin transparent carrier, which is robust and of very compact volume, and can be integrated into a cellular phone package, or other portable electronic device package, to form a complete standalone spectroscopic system for many application, for example, real-time spectroscopic measurements.

Figure 4:
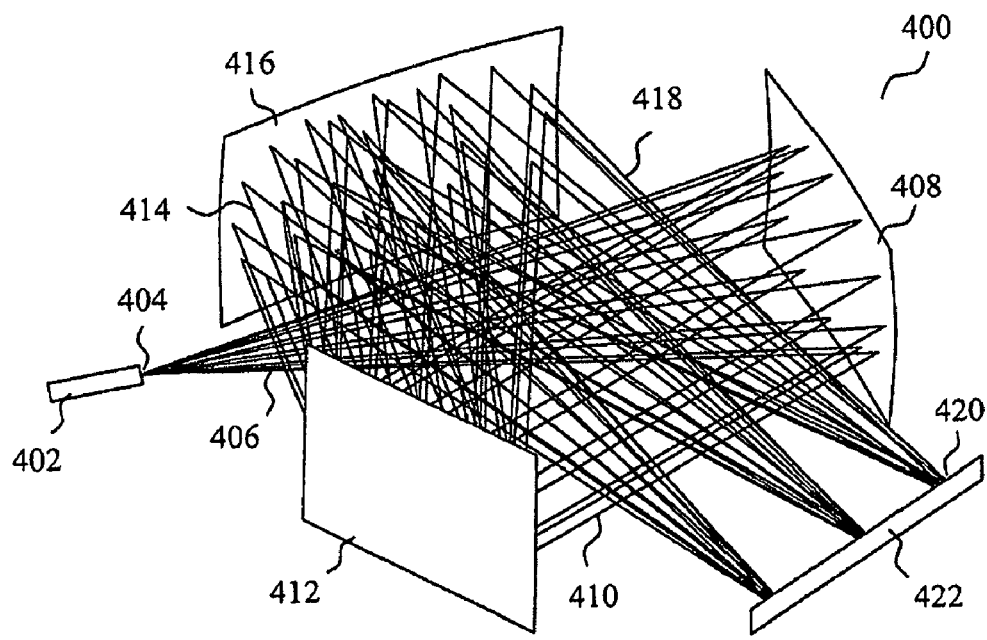
FIG. 4 shows perspective views of a mirror spectrometer of crossed Czerny-Turner configuration, where
Figure 4:
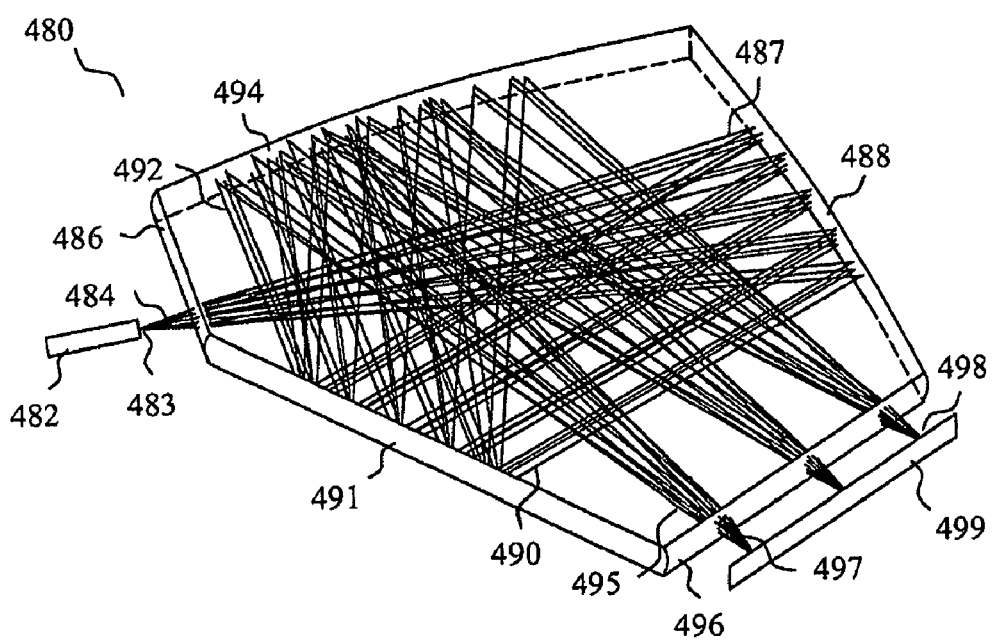

Next, referring to FIG. 4(a), another prior art of a mirror spectrometer of crossed Czerny-Turner geometry is illustrated in ray-trace form, which is designated by the general reference numeral 400. The spectrometer 400 is modified from the spectrometer 300 in FIG. 3(a), where the incident beam and the reflected beam from the diffraction grating cross. Its optics comprises an entrance aperture 404 that is the core of the optical fiber 402 for input signal delivery, a collimating mirror 408, a reflective diffraction grating 412 and a focusing mirror 416. For the spectrometer 400, the input light 406 emits from the entrance aperture 404 and propagates in divergence towards the collimating mirror 408, which collimates the divergent light 406 into the collimated light 410. The collimated light 410 propagates and is incident upon the grating 412, which disperses, in a reflective manner, the light 410 into the dispersive collimated light 414, and then the focusing mirror 416 focuses the light 414 into the convergent light 418 to form spectral images 420 on the detector 422. As shown in FIG. 4(a), the propagation paths for the divergent light 406, the collimated light 410, the dispersive light 414, and the convergent light 418 are all three-dimensional. The three key optical elements within the spectrometer 400, i.e. the collimating mirror 408, the grating 412 and the focusing mirror 416, must have finite working apertures large enough to accept and manipulate the light 406, 410, 414 and 418 without truncating them at any locations. As a result, the overall dimensional volume necessitated to construct the spectrometer 400 is three-dimensional, which is too large for being integrated into a cellular phone package, and very difficult or impossible to be reduced without sacrificing its performance characteristics.

In FIG. 4(b), one embodiment of the same mirror spectrometer of crossed Czerny-Turner geometry as shown in FIG. 4(a) is illustrated in ray-trace form based on the present invention, which is designated by the general reference numeral 480. The spectrometer 480 is constructed by combining its five key optical surfaces necessitated to build a compact spectrometer together with a single piece of monolithic transparent carrier. Its optics comprises an entrance aperture 483 that is the core of the optical fiber 482 for input signal delivery, a first cylindrical surface 486, a first cylindrical mirror 488, a reflective diffraction grating 491, a second cylindrical mirror 494 and a second cylindrical surface 496. For the spectrometer 480, the input light 484 emits from the entrance aperture 483 and propagates in divergence over a very short distance, then is intercepted by the first cylindrical surface 486, which collimates the divergent light 484 only in the tangential plane, converting it into a partially collimated light, i.e. the anamorphic light 487, which is collimated in the tangential plane, but remains divergent in the sagittal plane. The light 487 propagates and is intercepted by the first cylindrical mirror 488, which collimates it only in the sagittal plane, converting it into the fully collimated light 490. The light 490 continues to propagate and is incident upon the grating 491, which disperses, in a reflective manner, the light 490 into the dispersive collimated light 492. Upon being intercepted by the second cylindrical mirror 494, the light 492 is partially focused in the sagittal plane into the light 495, which is further partially focused by the second cylindrical surface 496 in the tangential plane into the fully convergent light 497 to form spectral images 498 on the detector 499. As shown in FIG. 4(b), the propagation paths for the anamorphic light 487, the collimated light 490, the dispersive light 492, and the anamorphic light 495 are all substantially two-dimensional. The five key optical surfaces within the spectrometer 480, i.e. the first cylindrical surface 486, the first cylindrical mirror 488, the grating 491, the second cylindrical mirror 494 and the second cylindrical surface 496, must have finite working aperture dimensions large enough only in the sagittal direction (horizontal), but very small aperture dimensions needed in the tangential direction (vertical), in order to accept and manipulate light 484, 487, 490, 492, 495 and 497 without truncating them at any locations. In practice, the tangential dimensions (vertical) of those key optical surfaces needed become a small fractions of their original values in the same prior art, for example, around ⅕~1/10 (i.e., an approximate reduction in size of 80% to 90% may be achieved) or even better. As a result, the overall dimensional volume necessitated to construct the spectrometer 480 is two-dimensional, or unilateral, which is significantly reduced compared with that of its prior art spectrometer without sacrificing its performance characteristics. Thus it is possible, based on the present invention, to easily construct a spectrometer fabricated with a single piece of thin transparent carrier, which is robust and of very compact volume, and can be integrated into a cellular phone package to form a complete standalone spectroscopic system for many application, for example, real-time spectroscopic measurements.

Figure 5:
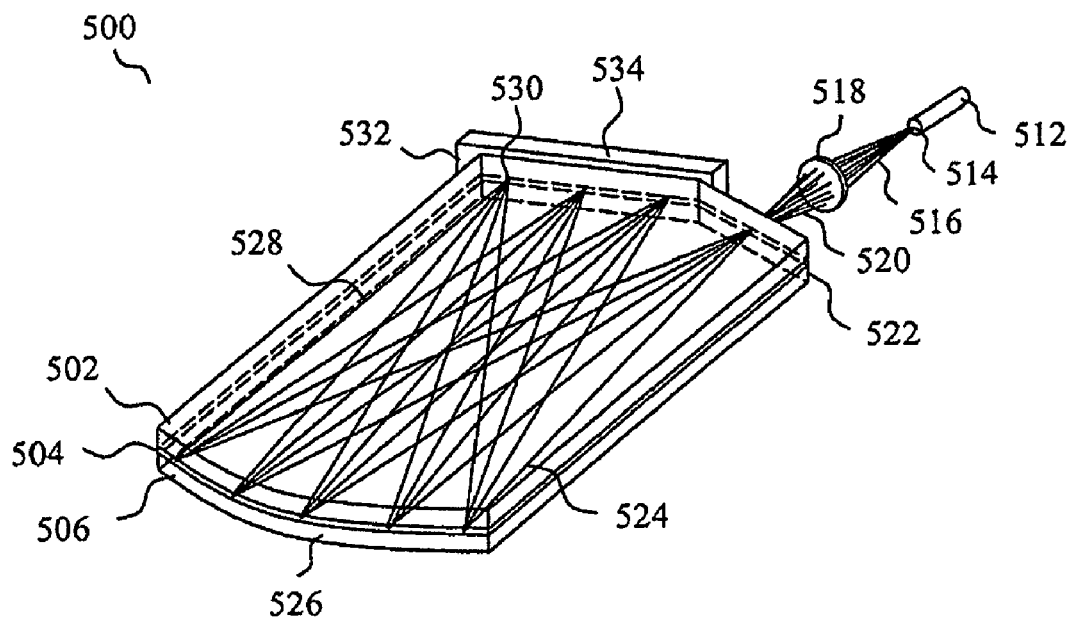
FIG. 5 shows two embodiments of compact spectrometers based on waveguide technology, which represent qualified candidates of compact spectrometers capable of being integrated into a spectrometer in the present invention.
Figure 5:
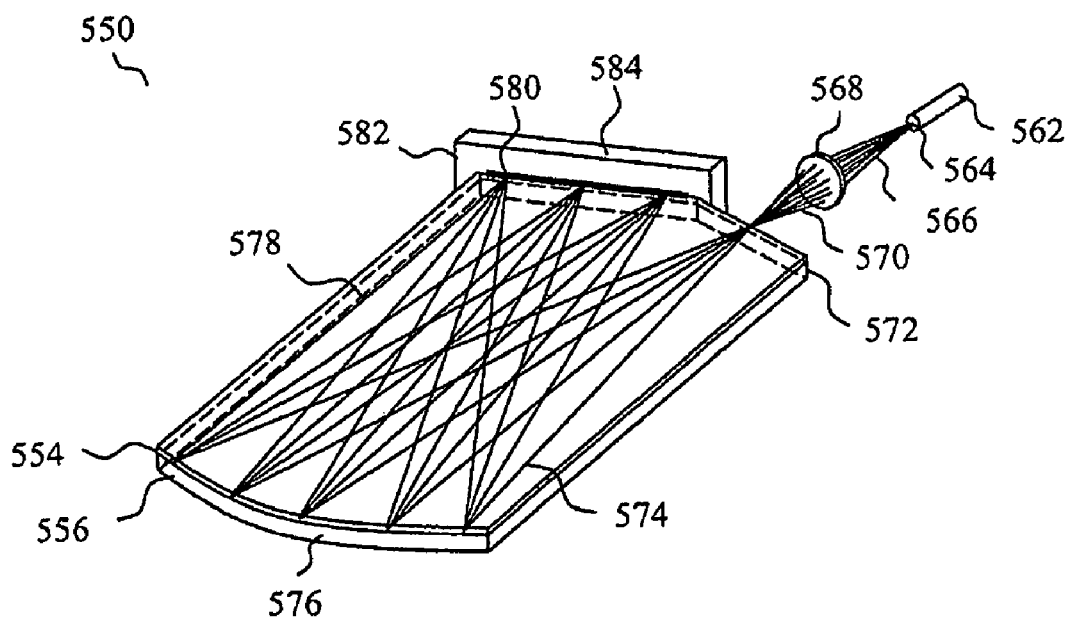

Next, referring to FIG. 5(a), where one embodiment of the candidate spectrometer based on waveguide technology is illustrated in the present invention, which is designated by the general reference numeral 500. It is constructed in a "sandwich" structure of three layers of glass: upper layer 502, middle layer 504 (very thin thickness of a ten to tens of microns) and lower layer 506, where 502 and 506 have refractive index lower than that of 504, all of which are combined together to form a single piece of monolithic transparent carrier. Its optics comprises an entrance aperture 514 that is the core of the optical fiber 512 (or a pinhole here) for input signal delivery, an input coupling lens 518, an upper waveguide interface between layer 502 and layer 504, a lower waveguide interface between layer 504 and layer 506, and a cylindrical reflective diffraction grating 526. For the spectrometer 500, the input light 516 emits from the entrance aperture 514 and propagates in divergence over a very short distance, then is intercepted by the coupling lens 518, which converts the divergent light 516 into the convergent light 520 and forms a 1:1 image of the entrance aperture 514 onto the input surface 522. After being coupled into the middle layer 504, the light 520 becomes an anamorphic divergent light 524, because its propagation path is confined in the tangential plane (vertical) by the total internal reflections occurring at the upper and lower waveguide interfaces, but unconfined divergent in the sagittal plane (horizontal). The light 524 continues to propagate and is incident upon the cylindrical grating 526, which disperses, in a reflective manner, the light 524 into the dispersive focused light 528, which forms the spectral images 530 upon arriving at the exiting and the detector surface 532, where the spectral images 530 have plural images laterally spread representing different wavelengths; vertically, each image point has a size equal to the thickness of the middle layer 504. As shown in FIG. 5(a), the propagation paths for the anamorphic light 524, the dispersive anamorphic light 528 are all substantially two-dimensional. The associated waveguide structure must have finite working aperture dimensions large enough only in the sagittal direction (horizontal), but very small aperture dimensions needed in the tangential direction (vertical), in order to accept and manipulate light 520, 524 and 528 to form spectral images. In practice, a few millimeters as the total tangential dimensions (vertical) of the "sandwich structure", i.e. the three optical glass layers, will be enough to provide a waveguide carrier body of the desired strength. As a result, the overall dimensional volume necessitated to construct the spectrometer 500 is substantially two-dimensional, or substantially unilateral. Thus it is possible, based on the present invention, to easily construct such a spectrometer fabricated with a waveguide substrate, which is robust and of very compact volume, and can be integrated into a cellular phone package, other portable electronic device package, to form a complete standalone spectroscopic system for many application, for example, real-time spectroscopic measurements.

FIG. 5(b) represents another embodiment similar to that of FIG. 5(a), where a spectrometer 550 is built with a waveguide structure of two layers: a thin middle layer 554 of higher refractive index and a thick lower layer 556 of lower refractive index. Here an upper waveguide interface exists between the air and layer 554, and a lower waveguide interface exists between layer 554 and layer 556. Its optics works in the same way as that of FIG. 5(a) and its propagation path is confined vertically in the tangential plane by the total internal reflections. This embodiment differentiates itself from that of FIG.

5(a) by the waveguide structure, herein the thin layer 554 is the light propagation layer fabricated by an approach different from that used for the spectrometer 500 in FIG. 5(a). The layer 556 is the main structure supporting substrate, and as long as it is strong enough for providing the desired strength, then it is possible, based on the present invention, to easily construct such a spectrometer fabricated with a waveguide substrate, which is robust and of very compact volume, and can be integrated into a cellular phone package, or other portable electronic device package, to form a complete standalone spectroscopic system for many application, for example, real-time spectroscopic measurements.

Figure 6:
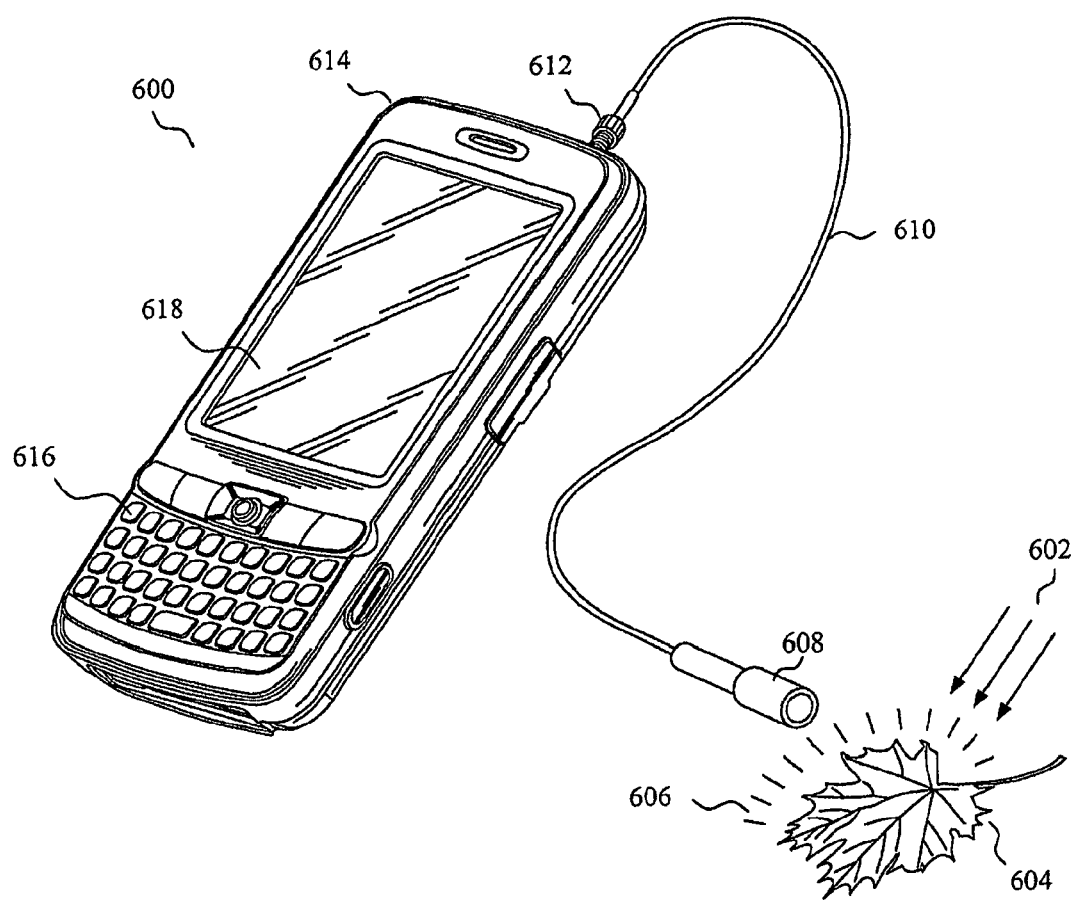
FIG. 6(a) shows an embodiment of a cellular phone integrated with a built-in miniature spectrometer in a process of real-time spectroscopic measurements.
FIG. 6(b) shows an embodiment of a cellular phone integrated with a built-in miniature spectrometer in a process of Raman spectroscopic measurements in medical application.
Figure 6:
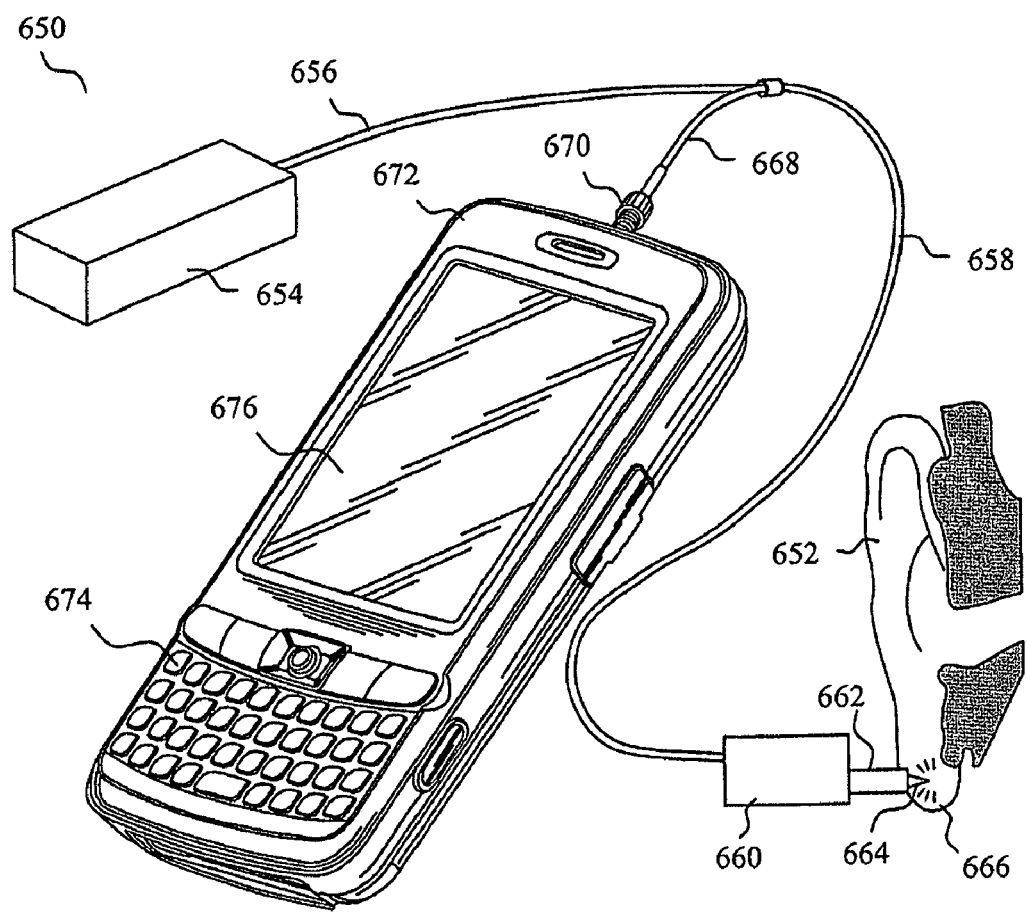

Next, referring to FIG. 6(a), an embodiment of a cellular phone integrated with a built-in miniature spectrometer is illustrated, which is designated by the general reference numeral 600. As a complete "spectrometer phone", it may have at least the following working modes: (1) wireless communication mode for making phone calls, browsing internet, sending/retrieving e-mails, transferring data, etc, (2) camera mode (if a digital camera is built in) for taking pictures, (3) PDA mode for functions of a computer, and (4) spectrometer mode for spectroscopic measurement. When the device is switched to the spectrometer mode, it is able to function as a truly standalone system for real-time spectroscopic measurements. In a typical such measurement, for example, the illuminating light 602 is shone on the sample 604, which reflects or radiates excited light 606 (depending on the nature of the incident light 602). The light 606 can be reflected light, or transmitted light, or excited fluorescent or Raman radiations in UV, or visible, or infrared spectral range (depending on applications). The fiber head 608 collects a portion of the light 606 and its focusing optics couples the input optical signals into the optical fiber 610. The fiber 610 is connected with the device 614 through the fiber connector 612, delivering input optical signals into the built-in spectrometer. Properly pressing buttons 616 to input different functioning commands by the operator, tasks of measurements like taking a spectrum, saving a spectrum, displaying a spectrum on the LCD window 618, etc, can be fulfilled accordingly. This "spectrometer phone" is a compact, standalone device and provides convenience of usage: the operator can hold the device 614 with one hand and use the other hand to handle and point the fiber head 608 to collect input optical signals 606. At any time after a spectrum is measured, it can be sent out in wireless communication to a remote station or another cellular phone user to share the measurement results right away, allowing instant data analyzing or information processing to be fulfilled, which is very critical in a wide range of applications.

Referring to FIG. 6(b), another embodiment of the same "spectrometer phone" used in a medical application is illustrated, which is designated by the general reference numeral 650. This health care monitoring system is used as a Raman spectrometer and can be used at a civilian's home. It comprises: the laser 654, the Raman fiber cable 658 and the "spectrometer phone" 672. The laser 654 can be a compact laser like a laser diode, which can be integrated in the "spectrometer phone" 672. The Raman cable 658 is a commercially available product from InPhotonics based on U.S. Pat. No. 5,122,127. When the phone 672 is switched to the spectrometer mode, it is able to function as a truly standalone system for health monitoring measurements. In a non-invasive blood glucose measurement, for example, the excitation light comes from the laser 654, which is delivered through the laser fiber channel 656 and the main fiber cable 658 to the optical head 660, where the output laser 664 is focused on the sample 652 through the lens in tube 662. Herein the sample 652 is a patient's ear and the laser spot 664 is focused on the earlobe, where more blood may generate stronger Raman signals. As the result of laser excitation, Raman signal light 666 from blood is excited. The lens in tube 662 collects a portion of the light 666, which is re-directed by the built-in dichroic filter inside optical head 660 and coupled into the signal channel inside cable 658, which is branched to signal fiber 668. The fiber 668 is connected with the device 672 through the fiber connector 670, delivering input Raman signals into the built-in spectrometer. Properly pressing buttons 674 to input different functioning commands by the operator, tasks of measurements like taking a spectrum, processing the spectrum, saving a spectrum, displaying a spectrum on the LCD window 676, etc, can be fulfilled accordingly. This "spectrometer phone" based Raman system is a compact, standalone device and provides convenience of usage for diabetes patients to carry out daily routine measurements of the blood glucose at home in a non-invasive manner. It offers significant advantages in reducing the cost and health risk, compared with other methods for fulfilling the same task. It can also be used to monitor other blood components like cholesterol in a non-invasive manner.

Figure 7:
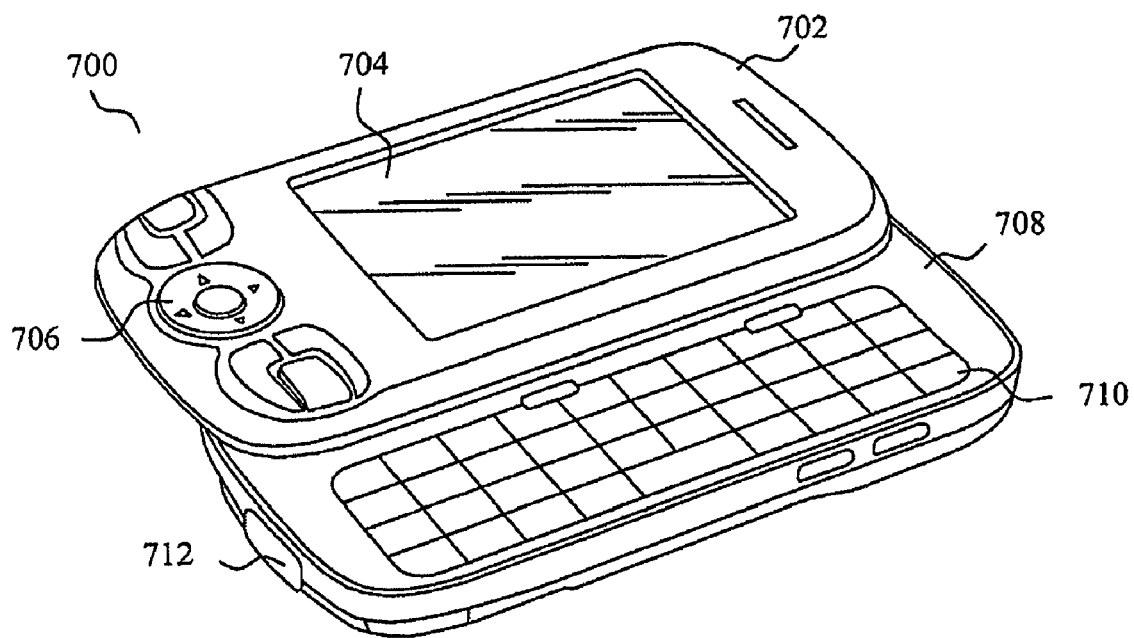
FIG. 7(a) represents a cellular phone capable of functioning as a platform.
FIG. 7(b) represents a compact spectrometer with a thin package.
FIG. 7(c) shows a cellular phone attached with such a compact spectrometer in a process of real-time spectroscopic measurements.
FIG. 7(d) shows a cellular phone attached with such a compact spectrometer in a process of Raman spectroscopic measurements in medical application.
Figure 7:
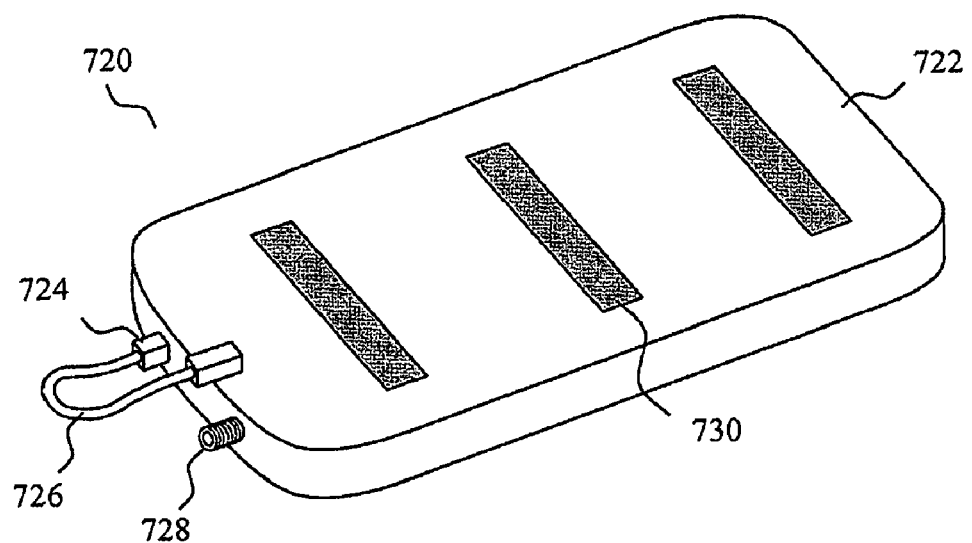
Figure 7:
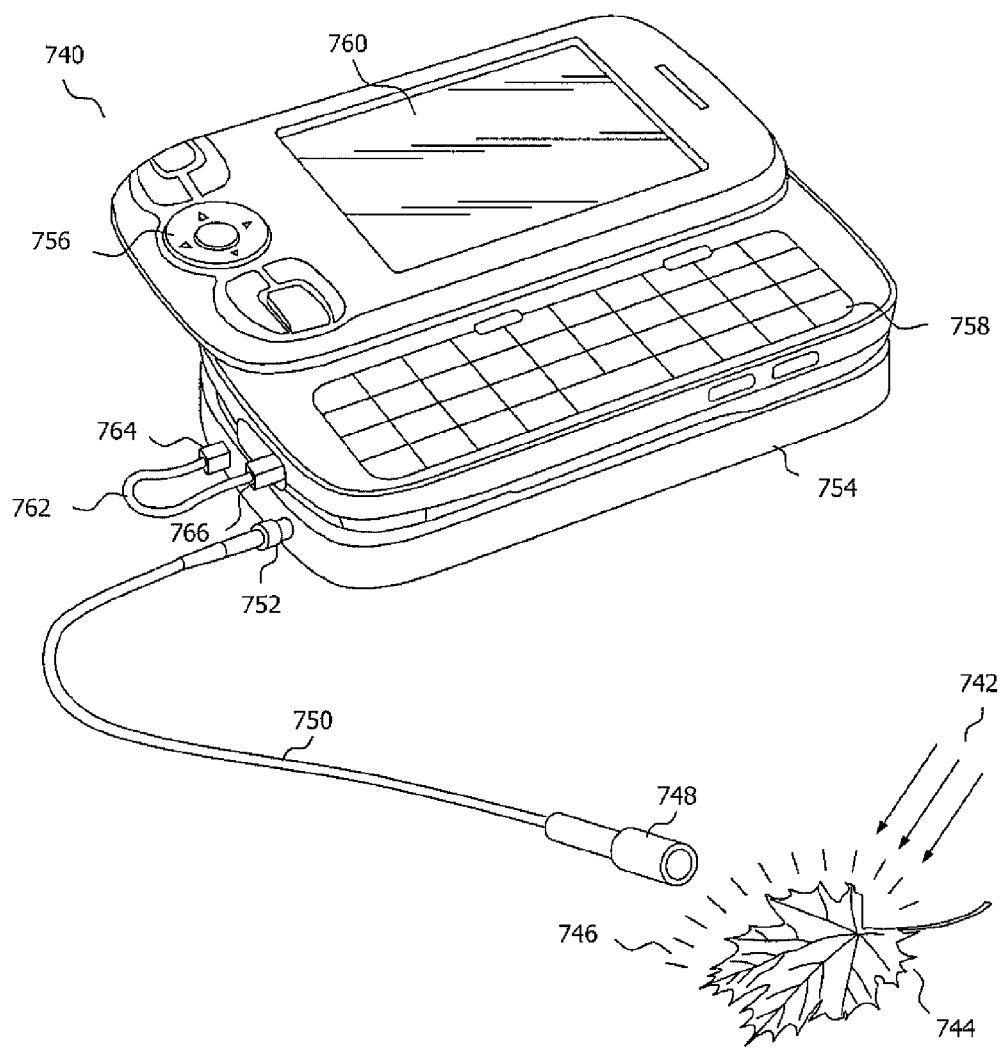
Figure 7:
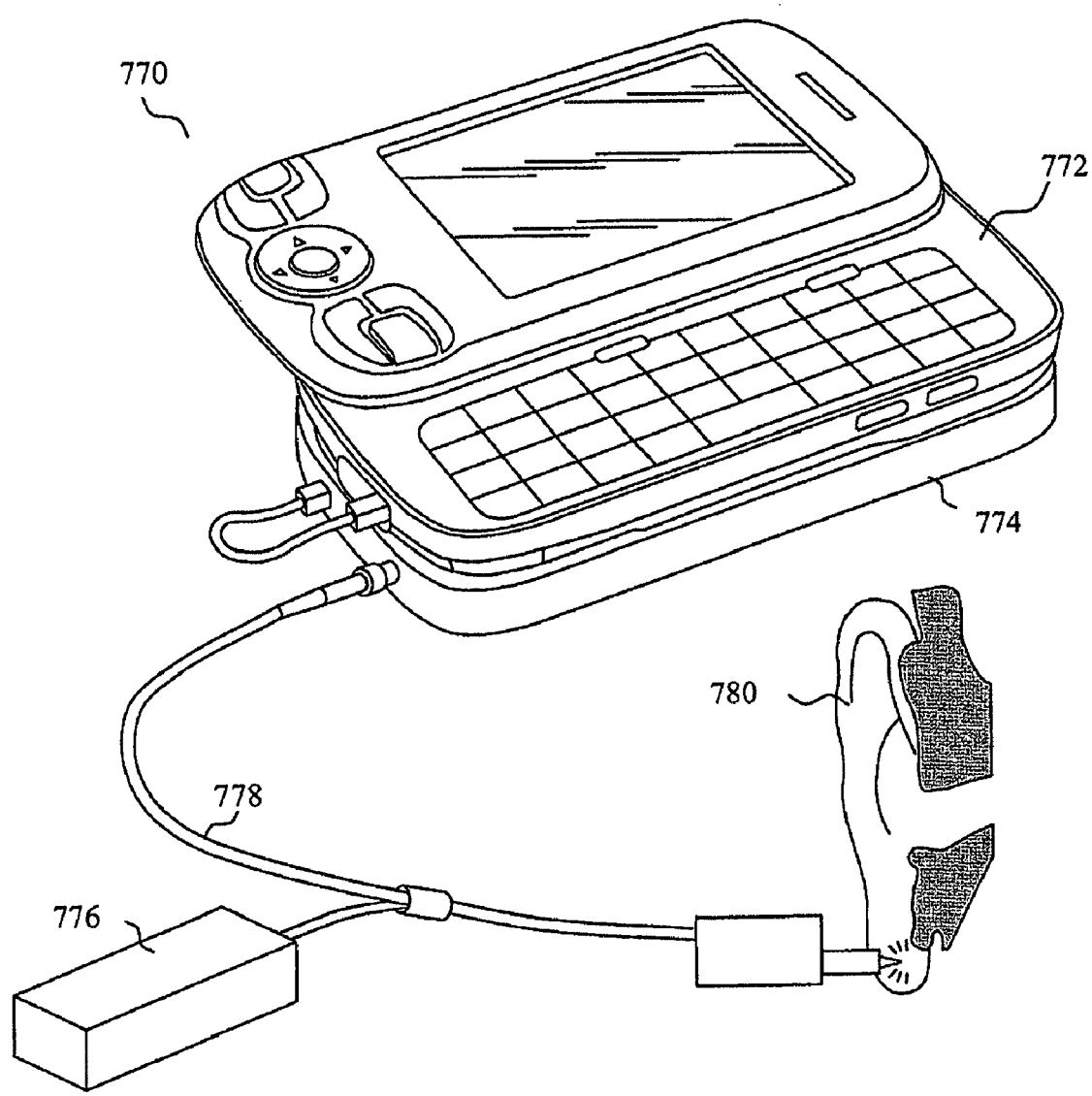

Next, referring to FIG. 7(a), a cellular phone at its slide out position with its keyboard exposed is illustrated, which is designated by the general reference numeral 700. As a "camera PDA phone" supporting multi functions, it may have at least the following working modes: (1) wireless communication mode for making phone calls, browsing internet, sending/retrieving e-mails, transferring data, etc, (2) camera mode for taking pictures, and (3) PDA mode for functions of a computer. It comprises: the top portion 702 which has LCD display window 704, function buttons 706, and bottom portion 708 which has keyboard 710 and I/O port 712 including an USB port.

Referring to FIG. 7(b), a compact spectrometer in the package based on the present invention is illustrated, which is designated by the general reference numeral 720. As a complete independent subsystem, its main body 722 has two ports to communicate with outside world: the USB port 724 where a USB cable 726 is connected, and fiber connection port 728 for optical inputs. The mechanical package of this compact spectrometer is very thin and has the same footprint of that of the "PDA phone" 700 shown in FIG. 7(a). There are three stripes of Velcro tapes 730 on the top surface of its main body 722 for attaching with the cellular phone 700.

Referring to FIG. 7(c), an embodiment of the same cellular phone 700 attached with the same compact spectrometer 720 by Velcro tapes is illustrated, which is designated by the general reference numeral 740. As a combined standalone system of "spectrometer plus phone", it has all those three working modes listed above plus a new mode: spectrometer mode for spectroscopic measurement, which is implemented by entering into PDA mode for functions of a computer and running an associated software to allow the phone 700 and the spectrometer 720 to communicate with each other via USB connection. USB connection is easily fulfilled via cable 762 connecting USB port 764 and USB port 766 at each end. When the device is switched to the spectrometer mode, the spectrometer 720 gets electrical power via USB connection from the phone 700, and will send measured electronic signals back to the phone 700 via USB connection as well. In a typical such measurement, for example, the incident light 742 is shone on the sample 744, which reflects or radiates excited light 746 (depending on the nature of the incident light 742). The fiber head 748 collects a portion of the light 746 and its focusing optics couples the input optical signals into the optical fiber 750. The fiber 750 is connected with the spectrometer 754 through the fiber connector 752, delivering input optical signals into the spectrometer. Properly pressing buttons 756 and keyboard 758 to input different functioning commands by the operator, tasks of measurements like taking a spectrum, saving a spectrum, displaying a spectrum on the LCD window 760, etc, can be fulfilled accordingly. This "spectrometer plus phone" becomes a compact, standalone device and provides convenience of usage: the operator can hold the unit 740 with one hand and use the other hand to handle and point the fiber head 748 to collect input optical signals 746. At any time after a spectrum is measured, it can be sent out in wireless communication to a remote station or another cellular phone user to share the measurement results right away, allowing instant data analyzing or information processing to be fulfilled, which is very critical in a wide range of applications.

Referring to FIG. 7(d), another embodiment of the same "spectrometer plus phone" shown in FIG. 7(c) used in a medical application is illustrated, which is designated by the general reference numeral 770. It comprises: the laser 776, the Raman fiber cable 778, the spectrometer 774 and the phone 772. The laser 776 can be a compact laser like a laser diode, which can be integrated in the spectrometer 774. The Raman cable 778 is a commercially available product from InPhotonics based on U.S. Pat. No. 5,122,127. This Raman spectrometer is used as a health care monitoring system and can be used at a civilian's home for non-invasive glucose monitoring in the same way as described in FIG. 6(b). This "spectrometer plus phone" based Raman system is a compact, standalone device and provides convenience of usage for diabetes patients to carry out daily routine measurements of the blood glucose at home in a non-invasive manner. It offers significant advantages in reducing the cost and health risk, compared with other methods for fulfilling the same task. It can also be used to monitor other blood components like cholesterol in a non-invasive manner.

What is claimed is:

1. A portable electronic device comprising:
   a wireless communications unit that transmits and receives information;
   a display unit;
   an input unit that allows a user to input information or commands;
   a processor (CPU); and
   a spectrometer that forms a spectrum of light distribution on a detection plane from an input light beam, wherein the spectrometer includes:
   (i) first collimating optics that collimates the input light beam in a vertical plane without collimating the input light beam in a horizontal plane that is substantially orthogonal to the vertical plane so as to produce a partially collimated light beam;
   (ii) light beam collimating-dispersing-focusing optics that produces a partially focused dispersed light beam from the partially collimated light beam, the partially focused dispersed light beam being focused in the horizontal plane without being focused in the vertical plane; and
   (iii) second focusing optics that focuses the partially focused dispersed light beam in the vertical plane to form the light distribution on the detection plane.

2. The portable electronic device of claim 1, further comprising:
   a processor-readable storage unit;
   a first program stored on the processor-readable storage unit, the first program allowing a user to toggle between at least two of the following modes:
   (a) a communication mode for at least one of transmitting information and receiving information;
   (b) a PDA mode for operating the portable electronic device as a computer; and
   (c) a spectrometer mode for at least one of spectroscopic measurement and spectroscopic analysis;
   a second program stored on the processor-readable storage unit, the second program measures and analyzes the light distribution on the detection plane under the condition that the program is executed; and
   a third program stored on the processor-readable storage unit, the third program allowing the user to communicate with external devices under the condition that the program is executed.

3. The portable electronic device of claim 1, wherein:
   the wireless communications unit communicates wirelessly with a remote station, thereby allowing for at least one of transmission of communication information to a third-party and reception of communication information from the third-party.

4. The portable electronic device of claim 3, wherein:
   the communication information includes information corresponding to at least one of spectroscopic measurement and spectroscopic analysis.

5. The portable electronic device of claim 1, wherein:
   the spectrometer receives input light corresponding to spectral signals via an input port, to which a coupling optics that focuses the input light beam may be connected, the coupling optics being one of a lens system and a mirror system.

6. The portable electronic device of claim 1, wherein:
   the spectrometer receives input light corresponding to spectral signals via an input port, to which a coupling optics that transmits the input light beam may be connected, the coupling optics being one of an optical fiber cable and a lens-fiber system.

7. The portable electronic device of claim 1, wherein:
   the spectrometer works with input light signals over at least one of the following spectral bands:
   (i) ultra-violet;
   (ii) visible;
   (iii) near infrared; and
   (iv) infrared.

8. The portable electronic device of claim 1, wherein:
   the spectrometer receives and measures input light signals which fall into at least one of the following kinds of electro-magnetic waves:
   (i) radiating from a source;
   (ii) reflected from an object or materials;
   (iii) transmitting through an object or materials;
   (iv) excited fluorescent radiation by a UV light or a laser from an object or materials; and
   (v) excited Raman radiation by a laser from an object or materials.

9. The portable electronic device of claim 1, wherein:
   the portable electronic device can be used to measure and monitor a user's blood glucose level, based on at least one of the following spectroscopic approaches:
   (i) NIR absorption technique; and
   (ii) Raman technique, either of which is performed through a certain part of a user's body.

10. The portable electronic device of claim 1, wherein:
the portable electronic device can be used to measure and monitor a user's blood cholesterols, based on at least one of the following spectroscopic approaches:
  (i) NIR absorption technique; and
  (ii) Raman technique either of which is performed through a certain part of a user's body.

11. The portable electronic device of claim 1, wherein:
the portable electronic device can be used to measure a color and a spectrum of the input light beam radiating from a source, or reflected from the object, or transmitting through the material, at a field site.

12. The portable electronic device of claim 1, wherein:
the portable electronic device can be used to fulfill spectroscopic measurements for identifying whether certain suspicious materials of interest exist at a field site, based on at least one of the following spectroscopic approaches:
  (i) NIR absorption technique;
  (ii) fluorescent technique; and
  (iii) Raman technique.

13. The portable electronic device of claim 1, wherein:
  (i) the first collimating optics comprises at least a lens surface or a mirror surface which is cylindrical, toroidal, or conic aspherical;
  (ii) the light beam collimating-dispersing-focusing optics comprises one or more of a lens surface, a mirror surface, or a diffraction grating surface, each of which are either planar, cylindrical, toroidal, or conic aspherical; and
  (iii) the second focusing optics comprises at least a lens surface or a mirror surface which is cylindrical, toroidal, or conic aspherical.

14. The portable electronic device of claim 13, further comprising:
a processor-readable storage unit;
a first program stored on the processor-readable storage unit, the first program allowing a user to toggle between at least two of the following modes:
  (a) a communication mode for at least one of transmitting information and receiving information;
  (b) a PDA mode for operating the portable electronic device as a computer; and
  (c) a spectrometer mode for at least one of spectroscopic measurement and spectroscopic analysis;
a second program stored on the processor-readable storage unit, the second program measures and analyzes the light distribution on the detection plane under the condition that the program is executed; and
a third program stored on the processor-readable storage unit, the third program allowing the user to communicate with external devices under the condition that the program is executed.

15. The portable electronic device of claim 13, wherein:
the wireless communications unit communicates wirelessly with a remote station, thereby allowing for at least one of transmission of communication information to a third-party and reception of communication information from the third-party.

16. The portable electronic device of claim 15, wherein:
the communication information includes information corresponding to at least one of spectroscopic measurement and spectroscopic analysis.

17. The portable electronic device of claim 13, wherein:
the spectrometer receives input light corresponding to spectral signals via an input port, to which a coupling optics that focuses the input light beam may be connected, the coupling optics being one of a lens system and a mirror system.

18. The portable electronic device of claim 13, wherein:
the spectrometer receives input light corresponding to spectral signals via an input port, to which a coupling optics that transmits the input light beam may be connected, the coupling optics being one of an optical fiber cable and a lens-fiber system.

19. The portable electronic device of claim 13, wherein:
the spectrometer works with input light signals over at least one of the following spectral bands:
  (a) ultra-violet;
  (b) visible;
  (c) near infrared; and
  (d) infrared.

20. The portable electronic device of claim 13, wherein:
the spectrometer receives and measures input light signals which fall into at least one of the following kinds of electro-magnetic waves:
  (a) radiating from a source;
  (b) reflected from an object or materials;
  (c) transmitting through an object or materials;
  (d) excited fluorescent radiation by a UV light or a laser from an object or materials; and
  (e) excited Raman radiation by a laser from an object or materials.

21. The portable electronic device of claim 13, wherein:
the portable electronic device can be used to measure and monitor a user's blood glucose level, based on at least one of the following spectroscopic approaches:
  (a) NIR absorption technique; and
  (b) Raman technique, either of which is performed through a certain part of a user's body.

22. The portable electronic device of claim 13, wherein:
the portable electronic device can be used to measure and monitor a user's blood cholesterols, based on at least one of the following spectroscopic approaches:
  (a) NIR absorption technique; and
  (b) Raman technique, either of which is performed through a certain part of a user's body.

23. The portable electronic device of claim 13, wherein:
the portable electronic device can be used to measure a color and a spectrum of the input light beam radiating from a source, or reflected from the object, or transmitting through the material, at a field site.

24. The portable electronic device of claim 13, wherein:
the portable electronic device can be used to fulfill spectroscopic measurements for identifying whether certain suspicious materials of interest exist at a field site, based on at least one of the following spectroscopic approaches:
  (a) NIR absorption technique;
  (b) fluorescent technique; and
  (c) Raman technique.

25. A system comprising:
(A) a portable electronic device that includes:
  a wireless communications unit that transmits and receives information,
  a display unit,
  an input unit that allows a user to input information or commands, and
  a processor (CPU); and (B) a spectrometer that forms a spectrum of light distribution on a detection plane from an input light beam, wherein
the spectrometer includes:
(i) first collimating optics that collimates the input light beam in a vertical plane without collimating the input light beam in a horizontal plane that is substantially orthogonal to the vertical plane so as to produce a partially collimated light beam;
(ii) light beam collimating-dispersing-focusing optics that produces a partially focused dispersed light beam from the partially collimated light beam, the partially focused dispersed light beam being focused in the horizontal plane without being focused in the vertical plane; and
(iii) second focusing optics that focuses the partially focused dispersed light beam in the vertical plane to form the light distribution on the detection plane.

26. The system of claim 25, wherein:
the portable electronic device further includes:
a processor-readable storage unit;
a first program stored on the processor-readable storage unit, the first program allowing a user to toggle between at least two of the following modes:
(a) a communication mode for at least one of transmitting information and receiving information;
(b) a PDA mode for operating the portable electronic device as a computer; and
(c) a spectrometer mode for at least one of spectroscopic measurement and spectroscopic analysis;
a second program stored on the processor-readable storage unit, the second program measures and analyzes the light distribution on the detection plane under the condition that the program is executed; and
a third program stored on the processor-readable storage unit, the third program allowing the user to communicate with external devices under the condition that the program is executed.

27. The system of claim 25, wherein:
the wireless communications unit communicates wirelessly with a remote station, thereby allowing for at least one of transmission of communication information to a third-party and reception of communication information from the third-party.

28. The system of claim 27, wherein:
the communication information includes information corresponding to at least one of spectroscopic measurement and spectroscopic analysis.

29. The system of claim 25, wherein:
the spectrometer receives input light corresponding to spectral signals via an input port, to which a coupling optics that focuses the input light beam may be connected, the coupling optics being one of a lens system and a mirror system.

30. The system of claim 25, wherein:
the spectrometer receives input light corresponding to spectral signals via an input port, to which a coupling optics that transmits the input light beam may be connected, the coupling optics being one of an optical fiber cable and a lens-fiber system.

31. The system of claim 25, wherein:
the spectrometer works with input light signals over at least one of the following spectral bands:
(i) ultra-violet;
(ii) visible;
(iii) near infrared; and
(iv) infrared.

32. The system of claim 25, wherein:
the spectrometer receives and measures input light signals which fall into at least one of the following kinds of electro-magnetic waves:
(i) radiating from a source;
(ii) reflected from an object or materials;
(iii) transmitting through an object or materials;
(iv) excited fluorescent radiation by a UV light or a laser from an object or materials; and
(v) excited Raman radiation by a laser from an object or materials.

33. The system of claim 25, wherein:
the system can be used to measure and monitor a user's blood glucose level, based on at least one of the following spectroscopic approaches:
(i) NIR absorption technique; and
(ii) Raman technique, either of which is performed through a certain part of a user's body.

34. The system of claim 25, wherein:
the system can be used to measure and monitor a user's blood cholesterols, based on at least one of the following spectroscopic approaches:
(i) NIR absorption technique; and
(ii) Raman technique either of which is performed through a certain part of a user's body.

35. The system of claim 25, wherein:
the system can be used to measure a color and a spectrum of the input light beam radiating from a source, or reflected from the object, or transmitting through the material, at a field site.

36. The system of claim 25, wherein:
the system can be used to fulfill spectroscopic measurements for identifying whether certain suspicious materials of interest exist at a field site, based on at least one of the following spectroscopic approaches:
(i) NIR absorption technique;
(ii) fluorescent technique; and
(iii) Raman technique.

37. The system of claim 25, wherein:
the spectrometer (B) is detachable from the portable electronic device (A).

38. The system of claim 25, wherein:
the spectrometer (B) is connected to the portable electronic device (A) by a communication cable that permits transmission of at least one of information and power.

39. The system of claim 25, wherein:
(i) the first collimating optics comprises at least a lens surface or a mirror surface which is cylindrical, toroidal, or conic aspherical;
(ii) the light beam collimating-dispersing-focusing optics comprises one or more of a lens surface, a mirror surface, or a diffraction grating surface, each of which are either planar, cylindrical, toroidal, or conic aspherical; and
(iii) the second focusing optics comprises at least a lens surface or a mirror surface which is cylindrical, toroidal, or conic aspherical.

40. The system of claim 39, wherein:
the portable electronic device further includes:
a processor-readable storage unit;
a first program stored on the processor-readable storage unit, the first program allowing a user to toggle between at least two of the following modes:
(a) a communication mode for at least one of transmitting information and receiving information;
(b) a PDA mode for operating the portable electronic device as a computer; and (c) a spectrometer mode for at least one of spectroscopic measurement and spectroscopic analysis;
a second program stored on the processor-readable storage unit, the second program measures and analyzes the light distribution on the detection plane under the condition that the program is executed; and
a third program stored on the processor-readable storage unit, the third program allowing the user to communicate with external devices under the condition that the program is executed.

41. The system of claim 39, wherein:
the wireless communications unit communicates wirelessly with a remote station, thereby allowing for at least one of transmission of communication information to a third-party and reception of communication information from the third-party.

42. The system of claim 41, wherein:
the communication information includes information corresponding to at least one of spectroscopic measurement and spectroscopic analysis.

43. The system of claim 39, wherein:
the spectrometer receives input light corresponding to spectral signals via an input port, to which a coupling optics that focuses the input light beam may be connected, the coupling optics being one of a lens system and a mirror system.

44. The system of claim 39, wherein:
the spectrometer receives input light corresponding to spectral signals via an input port, to which a coupling optics that transmits the input light beam may be connected, the coupling optics being one of an optical fiber cable and a lens-fiber system.

45. The system of claim 39, wherein:
the spectrometer works with input light signals over at least one of the following spectral bands:
(a) ultra-violet;
(b) visible;
(c) near infrared; and
(d) infrared.

46. The system of claim 39, wherein:
the spectrometer receives and measures input light signals which fall into at least one of the following kinds of electro-magnetic waves:
(a) radiating from a source;
(b) reflected from an object or materials;
(c) transmitting through an object or materials;
(d) excited fluorescent radiation by a UV light or a laser from an object or materials; and
(e) excited Raman radiation by a laser from an object or materials.

47. The system of claim 39, wherein:
the system can be used to measure and monitor a user's blood glucose level, based on at least one of the following spectroscopic approaches:
(a) NIR absorption technique; and
(b) Raman technique, either of which is performed through a certain part of a user's body.

48. The system of claim 39, wherein:
the system can be used to measure and monitor a user's blood cholesterols, based on at least one of the following spectroscopic approaches:
(a) NIR absorption technique; and
(b) Raman technique, either of which is performed through a certain part of a user's body.

49. The system of claim 39, wherein:
the system can be used to measure a color and a spectrum of the input light beam radiating from a source, or reflected from the object, or transmitting through the material, at a field site.

50. The system of claim 39, wherein:
the system can be used to fulfill spectroscopic measurements for identifying whether certain suspicious materials of interest exist at a field site, based on at least one of the following spectroscopic approaches:
(a) NIR absorption technique;
(b) fluorescent technique; and
(c) Raman technique.

51. A method of measuring spectral characteristics of an input light beam using a portable electronic device that is at least one of a spectrometer-phone device and a spectrometer-phone system, the method comprising:
inputting an input light beam into a spectrometer of the portable electronic device;
forming a spectrum of light distribution from the input light beam with the spectrometer of the portable electronic device;
collecting information relating to the spectrum of light distribution with a processor disposed in the portable electronic device;
collimating the input light beam with a first optical element disposed in the dispersion spectrometer, the first optical element collimating the light beam in a vertical plane without collimating the light beam in a horizontal plane that is substantially orthogonal to the vertical plane, to produce a partially collimated light beam;
producing a partially focused dispersed light beam from the partially collimated light beam, the partially focused dispersed light beam being focused in the horizontal plane without being focused in the vertical plane; and
focusing the partially focused dispersed light beam in the vertical plane with an optical clement disposed in the dispersion spectrometer, the optical element being different from au optical element that form the partially focused dispersed light beam, to form the light distribution.

52. The method of claim 51, further comprising:
executing at least one program that is stored on a processor-readable storage unit disposed in the portable electronic device, at least one program being chosen among a first program, a second program, and a third program;
wherein
the first program allows a user to toggle between at least two of the following modes:
(a) a communication mode for at least one of transmitting information and receiving information;
(b) a PDA mode for operating the portable electronic device as a computer; and
(c) a spectrometer mode for at least one of spectroscopic measurement and spectroscopic analysis;
the second program measures and analyzes the light distribution on the detection plane under the condition that the program is executed; and
the third program allows the user to communicate with external devices under the condition that the program is executed.

53. The method of claim 51, further comprising:
wirelessly communicating with a remote station, thereby allowing for at least one of transmission and reception of communication information between the portable electronic device and a third-party.

54. The method of claim 53, wherein:
the communication information includes information corresponding to at least one of spectroscopic measurement and spectroscopic analysis.

55. The method of claim 51, further comprising:
receiving input light corresponding to spectral signals via an input port in the spectrometer of the portable electronic device,
wherein a coupling optics that focuses the input light beam may be connected to the input port, the coupling optics being one of a lens system and a mirror system.

56. The method of claim 51, further comprising:
receiving input light corresponding to spectral signals via an input port in the spectrometer of the portable electronic device,
wherein a coupling optics that transmits the input light beam may be connected to the input port, the coupling optics being one of an optical fiber cable and a lens-fiber system.

57. The method of claim 51, further comprising:
receiving and measuring input light signals with the portable electronic device,
wherein the input light signals are over at least one of the following spectral bands:
(i) ultra-violet;
(ii) visible;
(iii) near infrared; and
(iv) infrared.

58. The method of claim 51, further comprising:
receiving and measuring input light signals with the portable electronic device,
wherein
the input light signals fall into at least one of the following kinds of electro-magnetic waves:
(i) radiating from a source;
(ii) reflected from an object or materials;
(iii) transmitting through an object or materials;
(iv) excited fluorescent radiation by a UV light or a laser from an object or materials; and
(v) excited Raman radiation by a laser from an object or materials.

59. The method of claim 51, further comprising:
measuring and monitoring a user's blood glucose level with the portable electronic device,
wherein at least one of the measurement and the monitor of the blood glucose level is based on at least one of the following spectroscopic approaches:
(i) NIR absorption technique; and
(ii) Raman technique, either of which is performed through a certain part of a user's body.

60. The method of claim 51, further comprising:
measuring and monitoring a user's blood cholesterols with the portable electronic device,
wherein at least one of the measurement and the monitor of the blood glucose level is based on at least one of the following spectroscopic approaches:
(i) NIR absorption technique; and
(ii) Raman technique either of which is performed through a certain part of a user's body.

61. The method of claim 51, further comprising:
measuring a color and a spectrum of the input light beam radiating from a source, or reflected from the object, or transmitting through the material, at a field site with the portable electronic device.

62. The method of claim 51, further comprising of:
fulfilling spectroscopic measurements for identifying whether certain suspicious materials of interest exist at a field site with the portable electronic device, based on at least one of the following spectroscopic approaches:
(i) NIR absorption technique;
(ii) fluorescent technique; and
(iii) Raman technique.

63. The method of claim 51, further comprising:
(A) the first collimating optical element comprises at least a lens surface or a mirror surface which is cylindrical, toroidal, or conic aspherical;
(B) a group of optical elements, used for producing a partially focused dispersed light beam from the partially collimated light beam in the horizontal plane, comprises one or more of a lens surface, a mirror surface, or a diffraction grating surface, each of which are either planar, cylindrical, toroidal, or conic aspherical; and
(C) the second focusing optical element comprises at least a lens surface or a mirror surface which is cylindrical, toroidal, or conic aspherical,

64. The method of claim 63, further comprising:
executing at least one program that is stored on a processor-readable storage unit disposed in the portable electronic device, at least one program being chosen among a first program, a second program, and a third program;
wherein
the first program allows a user to toggle between at least two of the following modes:
(a) a communication mode for at least one of transmitting information and receiving information;
(b) a PDA mode for operating the portable electronic device as a computer; and
(c) a spectrometer mode for at least one of spectroscopic measurement and spectroscopic analysis;
the second program measures and analyzes the light distribution on the detection plane under the condition that the program is executed; and
the third program allows the user to communicate with external devices under the condition that the program is executed.

65. The method of claim 63, further comprising:
wirelessly communicating with a remote station, thereby allowing for at least one of transmission and reception of communication information between the portable electronic device and a third-party.

66. The method of claim 65, wherein:
the communication information includes information corresponding to at least one of spectroscopic measurement and spectroscopic analysis.

67. The method of claim 63, further comprising:
receiving input light corresponding to spectral signals via an input port in the spectrometer of the portable electronic device,
wherein a coupling optics that focuses the input light beam may be connected to the input port, the coupling optics being one of a lens system and a mirror system.

68. The method of claim 63, further comprising:
receiving input light corresponding to spectral signals via an input port in the spectrometer of the portable electronic device,
wherein a coupling optics that transmits the input light beam may be connected to the input port, the coupling optics being one of an optical fiber cable and a lens-fiber system.

69. The method of claim 63, further comprising:
receiving and measuring input light signals with the portable electronic device, wherein the input light signals are over at least one of the following spectral bands:
(i) ultra-violet;
(ii) visible;
(iii) near infrared; and
(iv) infrared.

70. The method of claim 63, further comprising:
receiving and measuring light input signals with the portable electronic device,
wherein the input light signals fall into at least one of the following kinds of electro-magnetic waves:
(i) radiating from a source;
(ii) reflected from an object or materials;
(iii) transmitting through an object or materials;
(iv) excited fluorescent radiation by a UV light or a laser from an object or materials; and
(v) excited Raman radiation by a laser from an object or materials.

71. The method of claim 63, further comprising:
measuring and monitoring a user's blood glucose level with the portable electronic device,
wherein at least one of the measurement and the monitor of the blood glucose level is based on at least one of the following spectroscopic approaches:
(i) NIR absorption technique; and
(ii) Raman technique, either of which is performed through a certain part of a user's body.

72. The method of claim 63, further comprising:
measuring and monitoring a user's blood cholesterols level with the portable electronic device,
wherein at least one of the measurement and the monitor of the blood cholesterols level is based on at least one of the following spectroscopic approaches:
(i) NIR absorption technique; and
(ii) Raman technique either of which is performed through a certain part of a user's body.

73. The method of claim 63, further comprising:
measuring a color and a spectrum of the input light beam radiating from a source, or reflected from the object, or transmitting through the material, at a field site with the portable electronic device.

74. The method of claim 63, further comprising:
fulfilling spectroscopic measurements for identifying whether certain suspicious materials of interest exist at a field site with the portable electronic device, based on at least one of the following spectroscopic approaches:
(i) NIR absorption technique;
(ii) fluorescent technique; and
(iii) Raman technique.

75. The portable electronic device of claim 1, wherein the spectrometer is a thin piece of monolithic transparent material.

76. The system of claim 25, wherein the spectrometer is a thin piece of monolithic transparent material.

77. The method of claim 51, wherein the spectrometer is a thin piece of monolithic transparent material.

78. The portable electronic device of claim 13, wherein the spectrometer is a thin piece of monolithic transparent material.

79. The system of claim 39, wherein the spectrometer is a thin piece of monolithic transparent material.

80. The method of claim 63, wherein the spectrometer is a thin piece of monolithic transparent material.

* * * * *